US008812252B2

(12) United States Patent
Parilov et al.

(10) Patent No.: US 8,812,252 B2
(45) Date of Patent: Aug. 19, 2014

(54) DETERMINING THE INTERACTION BETWEEN ELECTROMAGNETIC RADIATION AND A MATERIAL BY UTILIZING TRANSITION MODULES

(75) Inventors: Evgueni Parilov, Brooklyn, NY (US); Mary J. Potasek, Princeton, NJ (US); Karl W. Beeson, Princeton, NJ (US)

(73) Assignee: Simphotek, Inc., Newark, NJ (US)

( * ) Notice: Subject to any disclaimer, the term of this patent is extended or adjusted under 35 U.S.C. 154(b) by 510 days.

(21) Appl. No.: 12/386,652

(22) Filed: Apr. 21, 2009

(65) Prior Publication Data
US 2010/0037173 A1 Feb. 11, 2010

Related U.S. Application Data

(60) Provisional application No. 61/124,909, filed on Apr. 21, 2008.

(51) Int. Cl.
*H01S 3/00* (2006.01)
*G06F 17/50* (2006.01)
*G01N 21/17* (2006.01)
(52) U.S. Cl.
CPC ............ *G01N 21/17* (2013.01); *G06F 2217/16* (2013.01); *G06F 17/5009* (2013.01)
USPC ............................................. 702/40; 359/334

(58) Field of Classification Search
USPC ......................................................... 702/40
See application file for complete search history.

(56) References Cited

U.S. PATENT DOCUMENTS

| | | | |
|---|---|---|---|
| 4,156,144 A * | 5/1979 | Pike et al. ................. | 250/423 P |
| 5,422,907 A * | 6/1995 | Bhargava ........................ | 372/68 |
| 6,611,372 B1 * | 8/2003 | Peyghambarian et al. | 359/341.1 |
| 7,949,480 B2 * | 5/2011 | Parilov et al. .................. | 702/40 |
| 2002/0171917 A1 * | 11/2002 | Lelic et al. ................ | 359/341.4 |
| 2003/0037322 A1 * | 2/2003 | Kodosky et al. ............. | 717/162 |
| 2006/0140636 A1 * | 6/2006 | Marazzi et al. ............... | 398/147 |
| 2006/0232779 A1 * | 10/2006 | Shaw ............................. | 356/436 |
| 2007/0290147 A1 * | 12/2007 | Parilov et al. .............. | 250/492.1 |
| 2008/0088915 A1 * | 4/2008 | Hayashi et al. ............... | 359/334 |

FOREIGN PATENT DOCUMENTS

WO WO 2005012925 A2 * 2/2005

* cited by examiner

*Primary Examiner* — Michael Nghiem
*Assistant Examiner* — Haidong Zhang
(74) *Attorney, Agent, or Firm* — Ward & Zinna, LLC

(57) ABSTRACT

The present invention is a method, a system and a software arrangement that can be used to determine the interaction between electromagnetic radiation and a material. The invention simplifies the process of determining the interaction by separating the complex process into a plurality of simple transition modules. Each transition module is associated with at least one parameter and represents an electronic transition in the material.

6 Claims, 29 Drawing Sheets

DETERMINING THE INTERACTION BETWEEN ELECTROMAGNETIC RADIATION AND A MATERIAL BY UTILIZING TRANSITION MODULES

CROSS-REFERENCE TO RELATED APPLICATION

This application claims priority from U.S. Patent Application Ser. No. 61/124,909, filed Apr. 21, 2008, the entire disclosure of which is incorporated herein by reference.

STATEMENT REGARDING FEDERALLY FUNDED RESEARCH

The present invention was developed, at least in part, using U.S. Government support under Contract No. FA9550-07-C-0073 awarded by the Air Force Office of Scientific Research. Therefore, the Federal Government may have certain rights in the invention.

TECHNICAL FIELD

The present invention is a method, a system and a software arrangement that can be used to determine the interaction between electromagnetic radiation and a material. The invention simplifies the process of modeling and calculating the interaction by separating the complex process into a plurality of simple computational transition modules. Each transition module is associated with at least one parameter and represents an electronic transition in the material.

BACKGROUND OF THE INVENTION

The development of new materials and devices for photonics-based applications generally requires an extremely lengthy and expensive process where molecular engineers, chemists, materials scientists and device designers conduct extensive laboratory measurements in multimillion dollar laboratories. The development cycle could be greatly accelerated if the promising materials are first designed on computer-aided-design (CAD) software and then tested via computer simulation. However, no user-friendly optical CAD-like software exists that can simulate the complex linear and nonlinear interactions that occur when light or other electromagnetic radiation interacts with highly nonlinear optical materials. In particular, no easy-to-use optical CAD software is available that can accurately model both electromagnetic radiation propagation through a material and simultaneously model light-induced transitions that occur between energy levels of the material, e.g., energy transfer or up-conversion.

Most of known traditional techniques for simulating the nonlinear response of materials to high intensity electromagnetic radiation or laser beams are both difficult to implement and computationally very expensive. The major disadvantage of conventional methods for computing photophysical processes in linear and nonlinear materials or devices is their limited applicability, since the methods are generally targeted for a specific range of kinetics, materials or devices. A minor change in the material characteristics or optical interactions can lead to a major rewriting of the software, or require a completely new algorithm and new program, which is very laborious and sometimes can require months to years to write and debug.

Moreover, traditional analysis techniques are not able to easily simulate materials having more than one composition or materials that are composed of layers of differing compositions. The task of simulating a composite or layered material whose constituents are modeled by different methods may take a significant amount of time to combine and debug different software pieces which in most of the cases lack interface compatibility.

In addition, traditional theoretical/numerical analyses of laser beam transmission through nonlinear absorbing materials usually have involved many simplifying assumptions that narrowly limited their general applicability. For example, most traditional propagation/transmission analyses neglect several molecular excited states that are needed to explain the experimental data, particularly at high incident energies. The methods usually are unable to simulate ultrashort laser pulses and multi-photon processes which are becoming increasingly important in light-material interactions.

Parilov and Potasek in U.S. patent application Ser. No. 11/559,093 disclose a method to calculate the interaction of electromagnetic radiation with a material using the concepts of computational absorption and relaxation blocks. However, U.S. patent application Ser. No. 11/559,093 does not disclose methods and systems for calculating the interaction of electromagnetic radiation with materials for the cases of electron transfer, energy transfer and up-conversion. All of the just mentioned phenomena cannot be modeled by absorption and relaxation blocks alone. Electron transfer is the transfer of an electron from a first molecule or optically responsive material to a second molecule or electron acceptor material. Energy transfer is the transfer of energy from a first electron in a first molecule or optically responsive material to a second electron in a second molecule or energy acceptor material. Up-conversion is an electronic process in which two energetically excited electrons exchange energy, wherein the first electron gains energy and goes to a higher energy level and the second electron loses an equal amount of energy and goes to a lower energy level. Also not disclosed in U.S. patent application Ser. No. 11/559,093 are methods, software applications and computer graphical user interfaces (GUIs) to allow a user to design an energy level diagram for a virtual material that includes electronic transitions between the energy levels and to subsequently simulate the interaction of electromagnetic radiation with the virtual material. Furthermore, calculations simulating the interaction of electromagnetic radiation with complex materials that have two or more different compositions or that have two or more layers with different compositions are also not disclosed in U.S. patent application Ser. No. 11/559,093.

It would be desirable to develop a method, system and software structure for simulating electromagnetic radiation interactions with materials that utilize graphical user interfaces to provide a visual representation of the material properties, to provide user manipulated icons to construct modified energy level diagrams for the materials, and to provide a visual representation and manipulated icons to visualize and build a virtual sample of a monolithic or layered material with layers possibly made of different compositions. Such graphical user interfaces would allow a user to utilize a unified approach to simulate complex optical processes in materials by dividing the complex interaction into a series of simple computational modules represented by icons that can be easily combined to simulate the interaction. Furthermore, it would be desirable to have a unified set of modules that include absorption processes, relaxation processes, electron transfer processes, energy transfer processes and up-conversion processes. It would also be desirable to simultaneously determine the electronic populations of the energy levels of the material and all its different composites and different layers, and to determine how the electromagnetic radiation propagates through the material while, at the same time, accounting for nonlinear optical effects in the material.

SUMMARY OF THE INVENTION

One embodiment of this invention is a computer-based method that uses an application program to analyze an interaction between electromagnetic radiation and a material. Electromagnetic radiation includes, but is not limited to, visible light, ultraviolet light, infrared light, x-rays and microwaves. Materials include, for example, organic, inorganic, crystalline, amorphous, metallic or dielectric materials. The material may have a single homogeneous layer or composition or the material may have two or more different layers or the material may have at least one layer that includes at least two different compositions.

The method includes the following steps: receiving at a computer first input information about a plurality of properties for the electromagnetic radiation; receiving at the computer from a graphical user interface second input information about a plurality of energy levels for the material; receiving at a computer from a graphical user interface third input information about a plurality of transition modules that describe electronic changes in the material; and determining with an application program executing on the computer the interaction between the electromagnetic radiation and the material by using the first input information, the second input information and the third input information.

The first input information can include, for example, the direction, the duration, the magnitude of the electric field as a function of the radial profile, the intensity of the electric field as a function of the radial profile and the wavelength of the electromagnetic radiation.

The plurality of transition modules can include at least one absorption transition module and at least one relaxation transition module, the absorption transition module being associated with at least one absorption parameter and corresponding to an absorption process in the material and the relaxation transition module being associated with at least one relaxation parameter and corresponding to a relaxation process in the material. The plurality of modules can also include electron transfer transition modules, energy transfer transition modules and energy transfer upconversion transition modules associated with at least one electron transfer parameter, at least one energy transfer parameter, and at least one energy transfer upconversion parameter, respectively.

Determining the interaction between the electromagnetic radiation and the material includes finding an electronic population of at least one of the plurality of energy levels or finding a transmission factor, an absorption factor or an emission factor for the electromagnetic radiation in the material.

An optional step of the method includes receiving at the computer fourth input information about a linear or nonlinear response of the material to the electromagnetic radiation. Then the step of determining the interaction between the electromagnetic radiation and the material uses the first input information, the second input information, the third input information, and the fourth input information.

Another embodiment of the invention uses a plurality of icons to represent the energy levels and transitions. Here again first input information about a plurality of properties of the electromagnetic radiation is received at the computer for use in the application program. The first information can include, for example, the direction, the duration, the magnitude of the electric field as a function of the radial profile, the intensity of the electric field as a function of the radial profile and the wavelength of the electromagnetic radiation.

Another step of this embodiment is for the computer to display on a computer screen a toolbox having a plurality of icons. The plurality of icons includes a first icon representing an energy level for the material and at least a second icon representing an element of a plurality of transition modules for the material. The second icon is associated with at least one parameter in the application program. The plurality of transition modules can include an absorption transition module, a relaxation transition module, an electron transfer transition module, an energy transfer transition module and an up-conversion transition module.

Another step of this method is for the computer to display a designer window on the computer screen. The designer window is configured to present the plurality of energy levels for the material and the plurality of transition modules for the material. If the material is a composite material with two or more different compositions or a layered material with at least two layers of different compositions, the corresponding sets of energy levels and sets of transition modules for each different layer/composition can be presented in one or more designer windows.

Another step of this method is for the computer to receive second input information for the application program. In this step, the user moves a copy of the first icon from the toolbox to the designer window, thereby signifying a change in the plurality of energy levels for the material. This change is received by the computer when it detects that the icon has been moved.

Another step of this method is for the computer to receive third input information for the application program. The user moves a copy of the second icon from the toolbox to the designer window, thereby signifying a change in the plurality of transition modules for the material. This change is received by the computer when it detects that the icon has been moved. When a new transition module is added to the plurality of transition modules, then at least one associated parameter is incorporated into the application program. For example, these parameters may be entered by the user into the application program in response to a series of prompts issued by the application program.

Following the additions of the first input information, the second input information and the third input information, the application program calculates the interaction between the electromagnetic radiation and the material. Calculating the interaction can include determining the electronic population for at least one of the plurality of energy levels and/or determining, for example, a transmission factor, an absorption factor or an emission factor for the electromagnetic radiation in the material.

A modified embodiment of this invention includes receiving fourth input information for the application program. The fourth input information can include, for example, information about a linear or nonlinear response of the material to the electromagnetic radiation. The application program then calculates the interaction of the electromagnetic radiation and the material using the first input information, second input information, the third input information and the fourth input information.

Another embodiment of this invention is a system for analyzing an interaction between electromagnetic radiation and a material. The system includes a processing arrangement for executing computer programs, a display unit having at least one display screen, a memory unit, and a storage unit that stores the results generated by the application program.

The memory unit of the system stores an application program that includes first executable instructions operable on the system for determining the interaction between the electromagnetic radiation and the material and second executable instructions operable on the system for displaying a graphical user interface on the display unit.

The graphical user interface includes the functionality to show a toolbox and a designer window on the display unit. The toolbox includes a plurality of icons. The plurality of icons includes a first icon representing an energy level for the material and at least a second icon representing an element of a plurality of transition modules for the material. An icon representing a transition module corresponds to an electronic transition in the material and is associated with at least one parameter in the application program.

The designer window is configured to present the plurality of energy levels for the material and the plurality of transition modules for the material. If the interaction involves two or more materials or involves a layered material having two or more compositions, the designer window can present the energy levels and transition modules for the two or more materials in one designer window or in multiple designer windows.

The graphical user interface allows the user to move a copy of the first icon from the toolbox to the designer window, thereby modifying within the designer window the plurality of energy levels. The graphical user interface also allows the user to move a copy of the second icon from the toolbox to the designer window, thereby modifying within the designer window the plurality of transition modules for the material. These movements of the icons from toolbox to designer window are detected by the computer and form part of the input received by the computer. At the same time, the parameters associated with the second icon are received by the computer and incorporated into the application program.

As a modification of this embodiment for a system, the processing arrangement can include a first processing unit for executing the first executable instructions operable on the system for determining the interaction between the electromagnetic radiation and the material and a second processing unit for executing the second executable instructions operable on the system for displaying the graphical user interface on the display unit.

Another embodiment of the invention is a set of icons for use on a graphical display of a computer to input information into the computer for an analysis of an interaction between electromagnetic radiation and a material. The set comprises at least two of the following icons: an energy level, an absorption transition module associated with at least one absorption parameter and corresponding to an absorption process in the material, a relaxation transition module associated with at least one relaxation parameter and corresponding to a relaxation process in the material, an electron transfer transition module associated with at least one electron transfer parameter and corresponding to an electron transfer process in the material, an energy transfer transition module associated with at least one energy transfer parameter and corresponding to an energy transfer process in the material and an up-conversion transition module associated with at least one up-conversion parameter and corresponding to an up-conversion process in the material.

Another embodiment of this invention is a software arrangement for analyzing an interaction between electromagnetic radiation and a material. The material may be a simple material having one composition or the material may have two or more different layers or the material may have at least one layer that has at least two different compositions.

The software arrangement includes the following: a first set of instructions, when executed by a processing arrangement, that is capable of receiving first input information about a plurality of properties for the electromagnetic radiation; a second set of instructions, when executed by the processing arrangement, that is capable of receiving second input information, provided by a user utilizing a graphical user interface, about a plurality of energy levels for the electromagnetic radiation; a third set of instructions, when executed by the processing arrangement, that is capable of receiving third input information, provided by a user utilizing a graphical user interface, about a plurality of transition modules that describe electronic changes in the material; and a core set of instructions, when executed by the processing arrangement, that is capable of determining the interaction between the electromagnetic radiation and the material by using the first input information, the second input information and the third input information. Determining the interaction includes determining an electronic population of at least one of the plurality of energy levels and/or determining a transmission factor, an absorption factor or an emission factor for the electromagnetic radiation in the material.

Optionally, the software arrangement can include a fourth set of instructions, when executed by the processing arrangement, that is capable of receiving fourth input information about a linear response or a nonlinear response of the material to the electromagnetic radiation. The core set of instructions, when executed by the processing arrangement, is then capable of determining the interaction between the electromagnetic radiation and the material by using the first input information, the second input information, the third input information and the fourth input information.

In addition, the processing arrangement optionally includes a first processing unit and a second processing unit. The first processing unit executes the core set of instructions that is capable of determining an electronic population of at least one of the plurality of energy levels or is capable of determining a transmission factor, an absorption factor or an emission factor for the electromagnetic radiation in the material. The second processing unit controls the graphical user interface.

BRIEF DESCRIPTION OF THE DRAWINGS

A more detailed understanding of the present invention, as well as other objects and advantages thereof not enumerated herein, will become apparent upon consideration of the following detailed description and accompanying drawings, wherein:

The upper portion of FIG. 1A illustrates a perspective view of a laser pulse directed to a block of material. The lower portion of FIG. 1A illustrates an expanded plan view of a small volume element dV shown in the upper portion of the figure. The expanded view schematically illustrates a group of chromophores.

In FIG. 7A, the designer window is blank. In FIG. 7B, a user has moved a first copy of an energy level icon into the designer window, causing a first energy level to be displayed. In FIG. 7C, a user has moved a second copy of an energy level icon into the designer window, causing a second energy level to be displayed. In FIG. 7D, a user has moved a copy of an absorption icon into the designer window, causing an absorption transition to be displayed. In FIG. 7E, a user has moved a copy of a relaxation icon into the designer window, causing a relaxation transition to be displayed.

DETAILED DESCRIPTION OF THE PREFERRED EMBODIMENTS

Figure 1A:
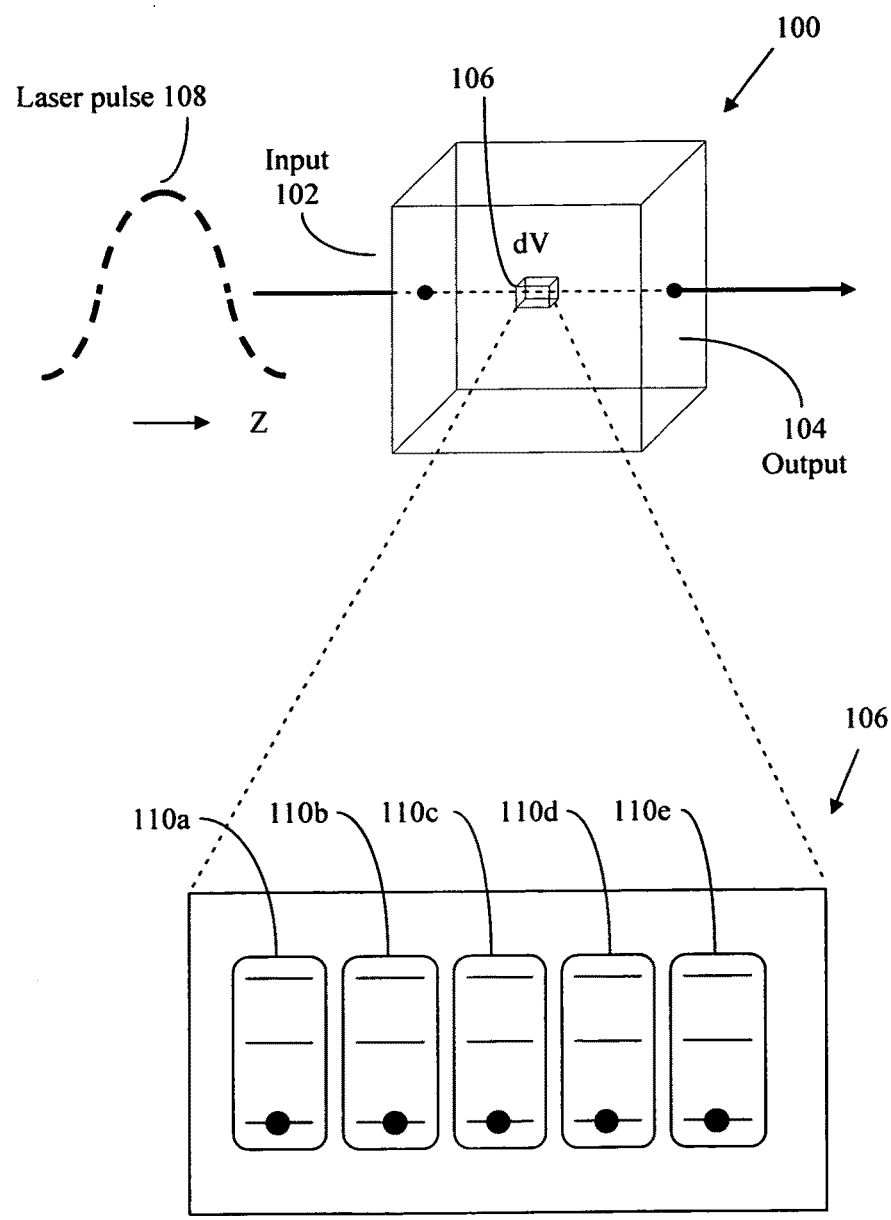
FIG. 1B is another plan view of the volume element dV illustrating three energy levels and one electron per chromophore.
FIG. 1C illustrates a schematic view of the volume element before the laser pulse enters the element.
FIG. 1D illustrates the volume element during the time that the laser pulse passes through the element.
FIG. 1E illustrates a material that has one layer and two compositions.
FIG. 1F illustrates a material that has two layers with different compositions.

The preferred embodiments of the present invention will be better understood by those skilled in the art by reference to the above listed figures. The preferred embodiments of this invention illustrated in the figures are not intended to be exhaustive or to limit the invention to the precise form disclosed. The figures are chosen to describe or to best explain the principles of the invention and its applicable and practical use to thereby enable others skilled in the art to best utilize the invention.

Embodiments of this invention include methods, a system and a software arrangement that can be used to determine the interactions between electromagnetic radiation and a material. Electromagnetic radiation includes, but is not limited to, visible light, ultraviolet light, infrared light, x-rays and microwaves.

Interactions between electromagnetic radiation and a material include linear optical and nonlinear optical interactions. Linear interactions include, but are not limited to, single photon absorption (SPA), radiative relaxation from a higher energy state to a lower energy state, non-radiative relaxation, linear dispersion, and diffraction. Nonlinear interactions include, but are not limited to, two-photon absorption (TPA), three-photon absorption (3PA), and absorption of more photons (multi-photon absorption MPA), electron transfer, energy transfer, up-conversion, the Kerr effect, nonlinear dispersion effects and effects resulting from a nonlinear index of refraction due to a $\text{Re}\chi^{(3)}$ effect, a $\text{Re}\chi^{(5)}$ effect or a $\text{Re}\chi^{(2n+1)}$ effect of higher order with n>1. The term $\text{Re}\chi^{(5)}$, for example, refers to the real part of the nonlinear susceptibility $\chi^{(5)}$.

Materials include any type of material that has a response to electromagnetic radiation. Example materials include organic materials, inorganic materials, crystalline materials amorphous materials, metals and dielectrics. The materials can be, for example, homogeneous materials that have one composition, composite materials that have two or more compositions or layered materials that have two or more different layers.

Example organic materials include organic chromophores that are in solution or that are embedded in optically inert solids. The chromophores can consist of a single type of molecules or multiple types. For example, chromophores of multiple types can be donor chromophores and acceptor molecules that can undergo electron transfer, energy transfer or energy up-conversion.

An example of a layered material is a material that has two layers having different compositions. The first layer can, for example, contain a material that exhibits optical self-focusing due to the nonlinear Kerr effect. The second layer can, for example, include an optical material that undergoes two-photon or three-photon absorption. The amount of two-photon or three-photon absorption that takes place in the second layer depends on the intensity of the light incident on the second layer. In this example, the material properties of the first layer can focus a light beam in the second layer and increase the probability of two-photon or three-photon absorption in the second layer.

Examples of inorganic materials include, for example, ionized dopant atoms that are embedded in an inert solid matrix. Such doped materials can be used as laser materials, fiber laser materials, fluorescent materials, phosphorescent materials, optical amplifiers and so forth. Other inorganic materials include quantum dot materials or quantum wire materials made from nanocrystals of inorganic semiconductors such as, for example, cadmium sulfide (CdS), cadmium selenide (CdSe), zinc sulfide (ZnS) or lead sulfide (PbS).

One illustrative example of an interaction of electromagnetic radiation with a material is shown schematically in FIGS. 1A-1F. FIG. 1A illustrates a laser pulse 108 directed toward the input surface 102 of a layer 100 of an optically responsive material. The laser pulse can pass through the material and exit the output surface 104, be partially absorbed by the material or be completely absorbed by the material. The material contains light absorbing elements that are dispersed in the material and that can absorb a portion of the laser beam.

In this illustrative example, the light absorbing elements are organic chromophores 110 that are dispersed in layer 100. A small volume element dV or 106 is illustrated in the upper portion of FIG. 1A. An expanded side plan view of volume element 106 is shown in the lower portion of FIG. 1A and in FIG. 1B. For simplicity, five chromophores 110a, 110b, 110c, 110d and 110e being in the same energy state are illustrated.

Figure 1B:
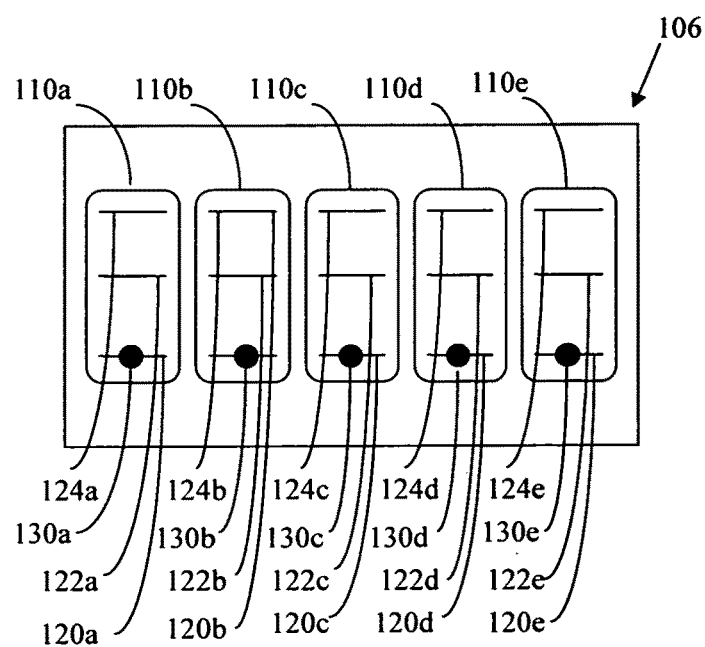

FIG. 1B illustrates the energy level diagrams (Jablonski state diagrams) of the chromophores in volume element 106. Chromophore 110a has three energy levels, ground state 120a, first excited state 122a and second excited state 124a. Chromophore 110a has an electron 130a in the ground state 120a. Chromophore 110b has three energy levels, ground state 120b, first excited state 122b and second excited state 124b. Chromophore 110b has an electron 130b in the ground state 120b. Chromophore 110c has three energy levels, ground state 120c, first excited state 122c and second excited state 124c. Chromophore 110c has an electron 130c in the ground state 120c. Chromophore 110d has three energy levels, ground state 120d, first excited state 122d and second excited state 124d. Chromophore 110d has an electron 130d in the ground state 120d. Chromophore 110e has three energy levels, ground state 120e, first excited state 122e and second excited state 124e. Chromophore 110e has an electron 130e in the ground state 120e. While the energy levels illustrated in FIGS. 1A-1D are electronic energy levels, in other applications of the invention they could also be vibrational energy levels or rotational energy levels.

Figure 1C:
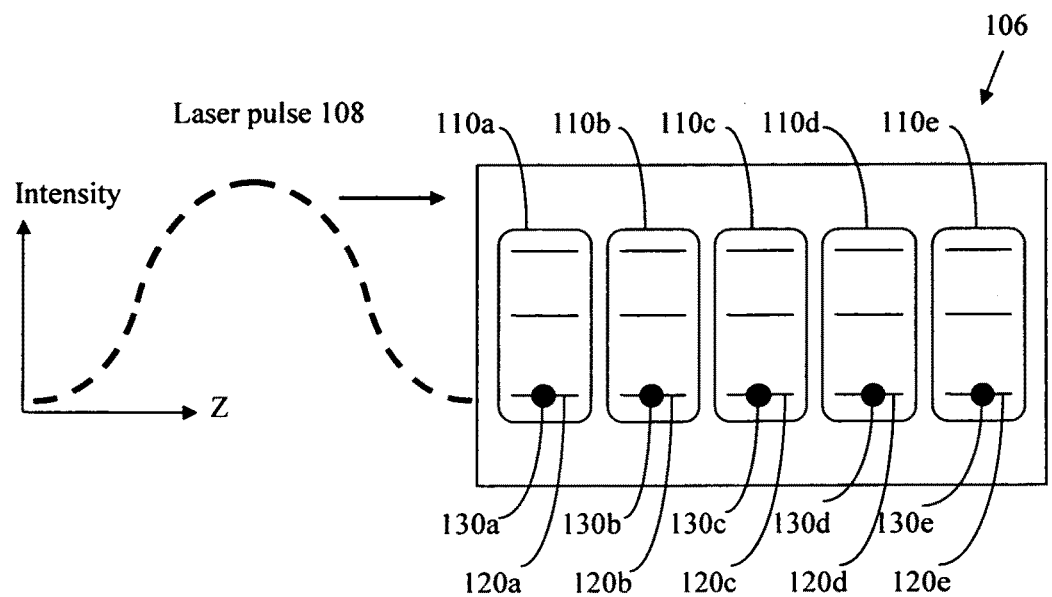

FIG. 1C illustrates a side plan view of volume element 106 just before the laser pulse 108 reaches the volume element. All the electrons, 130a, 130b, 130c, 130d and 130e, are in their respective ground states, 120a, 120b, 120c, 120d and 120e.

Figure 1D:
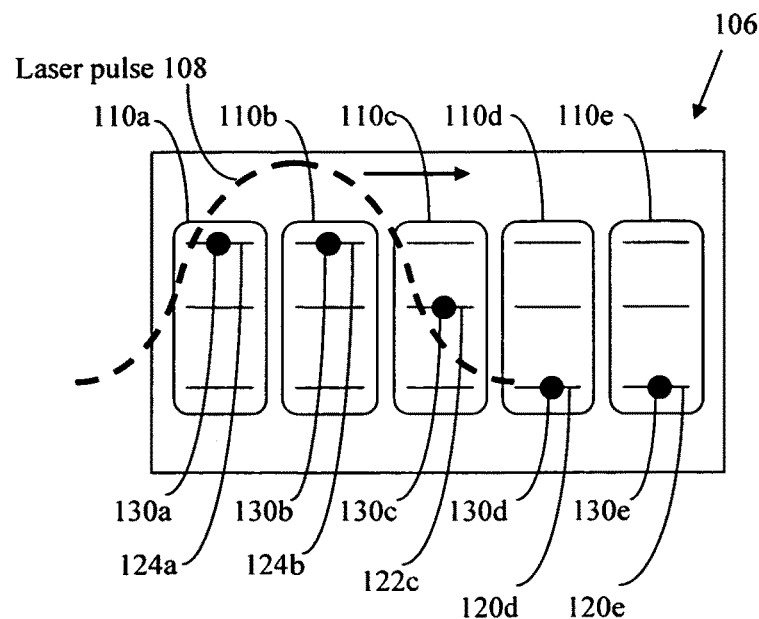

FIG. 1D illustrates a side plan view of volume element 106 as the laser pulse is passing through the volume element. Electron 130a in chromophore 110a has been excited to the second excited state 124a by the laser pulse. Electron 130b in chromophore 110b has also been excited to the second excited state 124b. At chromophore 110c, the laser pulse is less intense and the electron 130c is excited only to the first excited state 122c. The laser pulse has not yet reached chromophores 110c and 110e and the electrons 130d and 130e remain in the ground states of the chromophores.

Figure 1E:
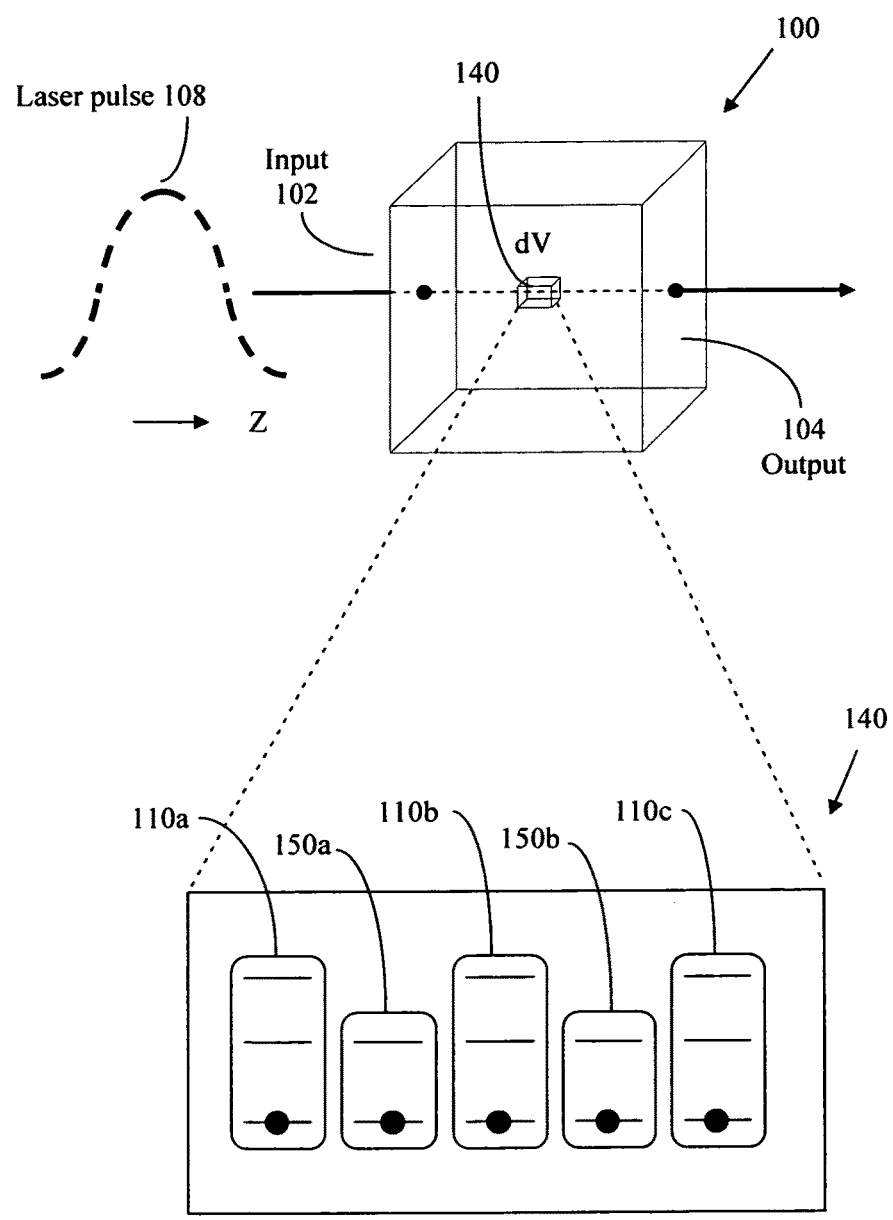

FIG. 1E illustrates a layer 100 of material containing volume element 140. As illustrated in an expanded plan view of volume element 140, layer 100 is a composite material containing two types of chromophores, chromophores 110b, 110b and 110c of a first type and chromophores 150a and 150b of a second type, different from the first type. Laser pulse 108 may excite one or both types of chromophores, but the optical response of the two types may be different. It is also within the scope of this invention that the composite material may contain more than two types of chromophores.

Figure 1F:
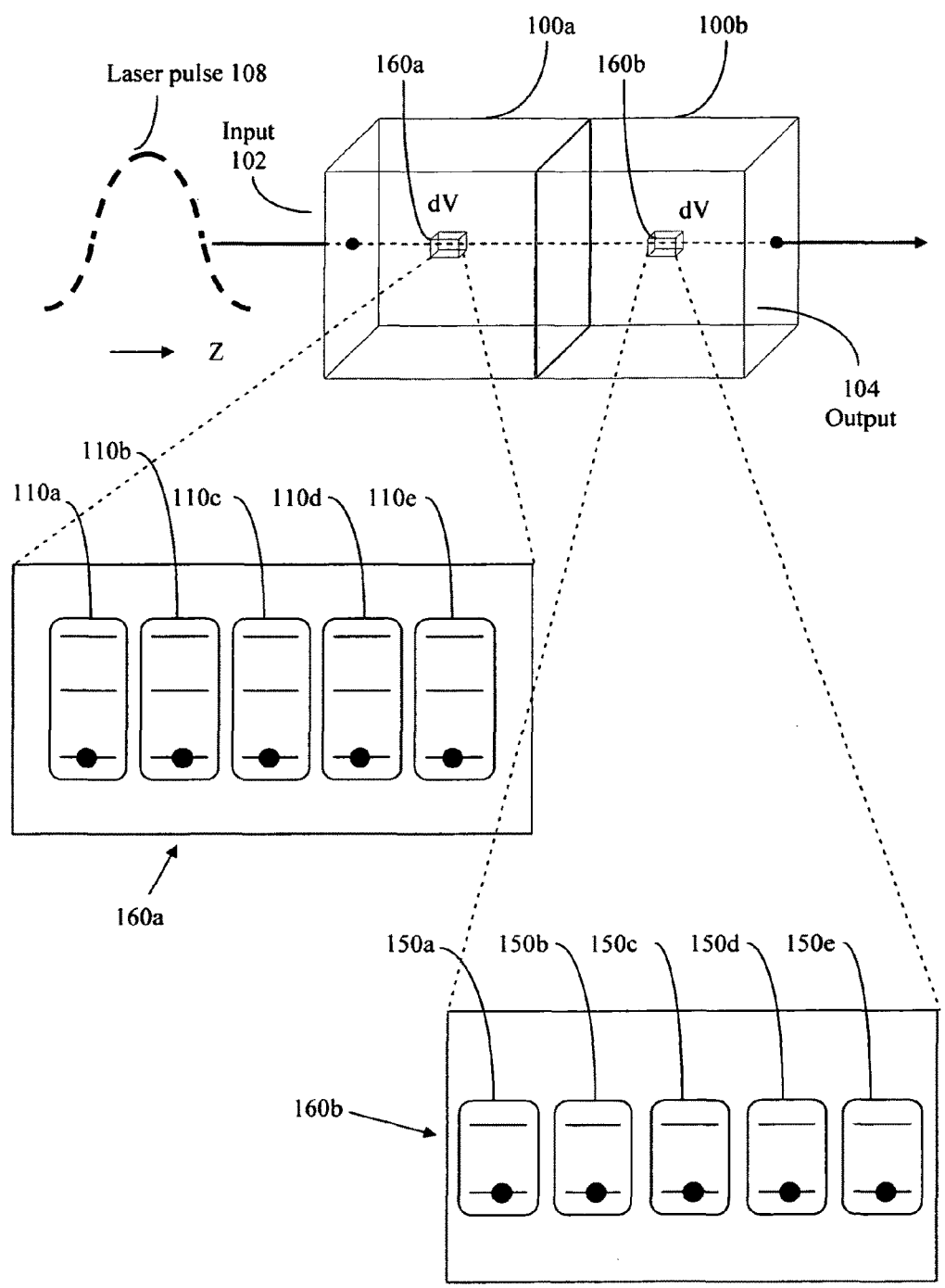

FIG. 1F illustrates a material that includes two layers, layer 100a and layer 100b. Layer 100a contains one type of chromophore, shown in the expanded plan view of volume element 160a as chromophores 110a, 110b, 110c, 110d and 110e. Layer 100b contains a second type of chromophore, shown in the expanded plan view of volume element 160b as chromophores 150a, 150b, 150c, 150d and 150e. It is also within the scope of this invention that the material may include more than two layers and each layer may contain more than one type of chromophore.

To describe the interaction of the laser pulse 108 with the material in layer 100 requires solving both the electromagnetic field equations of the laser pulse as it passes through the material and is partially absorbed and also solving the rate equations for the dynamics of the electron populations of the chromophores in the material. One set of partial differential equations (PDEs) describes evolution of the electromagnetic field of the laser pulse and another set of partial differential equations describes the rate equations for the electronic populations. Each set of equations may include linear and nonlinear processes. Both sets of equations must be solved simultaneously in order to describe the interaction of the electromagnetic radiation and the material. The equations are solved by applying a version of a symmetric split-step beam propagation method that is coupled to the Crank-Nicholson technique.

The methods and procedures to solve these equations are very time consuming and complex. There are no user-friendly methods in the prior art to determine such radiation-material interactions. The methods, software arrangement and system of this invention greatly simplify the process for determining the interaction of electromagnetic radiation with materials.

The background mathematical methods used in this invention will now be summarized.

A propagation of electric field E(z,r,t) along z-axis, denoted by $E(z,r,t)_z$, may be described by the following scalar form of Maxwell wave equations:

$$\left[\nabla^2 - \frac{1}{c_0^2}\partial_u^2\right]E(z, r, t)_z - \frac{1}{\varepsilon_0 c_0^2}\partial_u^2 P_l(z, r, t)_z \frac{1}{\varepsilon_0 c_0^2}\partial_u^2 P_{NL}(z, r, t)_z, \quad (1)$$

where $\varepsilon_0$ is the electric permittivity, $c_0$ is the light speed in vacuum, r is the distance to the center of the field along xy-plane, and the polarization vector P(z,r,t) was broken into its linear part $P_l$ and the nonlinear part $P_{NL}$:

$$P_l(t)_z = \varepsilon_0 \left(\int_{-\infty}^{t} \overline{\chi}^{(1)}(t-t') \cdot E(t')\,dt'\right)_z \quad (2)$$

-continued $$P_{NL}(t)_z = \varepsilon_0 \Bigg( \int_{-\infty...t} \int_{-\infty...t} \int_{-\infty...t} \vec{\chi}^{(3)}(t-t_1, t-t_2, \quad (3)$$
$$t-t_3) \vdots E(t_1)E(t_2)E(t_3)dt_1 dt_2 dt_3 +$$
$$\int\int\int_{(-\infty...t)^5} \vec{\chi}^{(5)}(t-t_1, t-t_2, t-t_3, t-t_4, t-t_5) \vdots E(t_1) \times$$
$$E(t_2)E(t_3)E(t_4)E(t_5)dt_1 dt_2 dt_3 dt_4 dt_5 + \ldots \Bigg)$$

By assuming that that susceptibility tensors $\vec{\chi}^{(1)}$, $\vec{\chi}^{(3)}$, $\vec{\chi}^{(5)}$, etc. are degenerate with the only non-trivial components $\chi^{(1)}_{==}$, $\chi^{(3)}_{===}$, $\chi^{(5)}_{====}$, etc., correspondingly, and that $\chi^{(3)}_{===}$, $\chi^{(5)}_{====}$, etc. are instantaneous, the polarization terms become $$P_l(t)_z = \varepsilon_0 \int_{-\infty}^t \vec{\chi}^{(1)}(t-t')E(t')_z dt' \quad (4)$$

$$P_{NL}(t)_z = \varepsilon_0 \left[ \sum_{\gamma=1}^{N_\chi} \chi^{(2\gamma+1)} E^{2\gamma+1}(t)_z \right] \quad (5)$$

The field and the nonlinear polarization terms are represented by their slowly varying envelope approximation (SVEA):

$$E(z,r,t)_z = E(z,r,t)\exp(ik_0 z - i\omega_0 t) + c.c. \quad (6)$$

$$P_{NL}(z,r,t)_z = P(z,r,t)\exp(ik_0 z - i\omega_0 t) + c.c. \quad (7)$$

The wave equation (1) in the frequency domain for the field and polarization envelopes become $$\left[ \nabla_\perp^2 + \left( \frac{\partial}{\partial z} + ik_0 \right)^2 + \quad (8) \right.$$
$$\left. \varepsilon(\omega)\frac{\omega^2}{c_0^2} \right] \tilde{E}(z, r, \omega - \omega_0) + \frac{\omega^2}{\varepsilon_0 c_0^2} \tilde{P}(z, r, \omega - \omega_0) = 0,$$

where $$k_0 = n(\omega_0)\frac{\omega_0}{c}, \quad (9)$$

$$\varepsilon(\omega) = 1 + \tilde{\chi}^{(1)}(\omega), \quad (10)$$

$$\tilde{E}(z, r, \omega) = \int_{-\infty}^\infty E(z, r, t)e^{i\omega t} dt \quad (11)$$

(same for $\tilde{P}$), $$\tilde{E}(z, r, \omega)_z = \tilde{E}(z, r, \omega - \omega_0)\exp(ik_0 z) + c.c. \quad (12)$$

(same for $\tilde{P}_{NL}(z, r, \omega)_z$).

By Expanding the Function $$k(\omega) = \sqrt{\varepsilon(\omega)}\omega/c_0 \quad (13)$$

into a Taylor series around central frequency $\omega_0$, equation (8) becomes as follows in the time domain:

$$\left[ \nabla_\perp^2 + \left( \frac{\partial}{\partial z} + ik_0 \right)^2 + \quad (14) \right.$$

$$\left. \left( \sum_{n=0}^\infty \frac{k^{(n)}(\omega_0)}{n!}(i\partial_t)^n \right)^2 \right] E(z, r, t) + \frac{1}{\varepsilon_0 c_0^2}(i\partial_t + \omega_0)^2 P(z, r, t) = 0.$$

If one defines the first two terms of the Taylor expansion as $$k^0(\omega_0) = k_0 + i\alpha_0/2, k^1(\omega_0) = k_1 + i\alpha_1/2, \quad (15)$$

and accumulates the tail of the expansion under one variable $$\hat{k} = i\alpha_0/2 - \alpha_1 \partial_t/2 + \Sigma_{n=2} k^{(n)}(\omega_0)(i\partial_t)^n/n! \approx i\alpha_0/2 - k_2 \partial_t^2/2 + o(\partial_t^3), \quad (16)$$

then Eq. (14) becomes $$[\nabla_\perp^2 + (\partial_z + 2ik_0 - k_1\partial_t + i\hat{k}) \quad (17)$$
$$(\partial_z + k_1\partial_t - i\hat{k})]E(z, r, t) + \frac{1}{\varepsilon_0 c_0^2}(i\partial_t + \omega_0)^2 P(z, r, t) = 0.$$

In the Moving Frame $$T = t - k_1 z, \xi = z \quad (18)$$

after applying certain simplifications, equation (17) becomes $$\partial_\xi E(\xi, r, T) \approx \left[ i\hat{k} + \frac{i}{2k_0}(1 + i\partial_T/\omega_0)^{-1}\nabla_\perp^2 \right] E(\xi, r, T) + \quad (19)$$
$$\frac{i}{2k_0}\frac{\omega_0^2}{\varepsilon_0 c_0^2}(1 + i\partial_T/\omega_0)P(\xi, r, T),$$

if $k_1 \approx k_0/\omega_0$ is assumed. Equation can be even more simplified to become as follows $$\partial_\xi E(\xi, r, T) \approx \left[ -\frac{\alpha_0}{2} + \frac{i}{2k_0}\nabla_\perp^2 \right] E(\xi, r, T) + \quad (20)$$
$$\frac{i}{2k_0}\frac{\omega_0^2}{\varepsilon_0 c_0^2}(1 + i\partial_T/\omega_0)P(\xi, r, T),$$

when the following inequalities hold $$|\partial_z E| << k_0|E|, |\partial_t E| << \omega_0|E|; \quad (21)$$

the same relationships hold for P.

By using the expression for nonlinear polarization $P_{NL}(t)_z$ given by Eq. (5), one can derive that the polarization envelope equals $P(T)_z = \varepsilon_0 E(T)[3\chi^{(3)}|E(T)|^2 + 10\chi^{(5)}|E(T)|^4 + \ldots]$. If we assume that $(1 + i\partial_T/\omega_0)E(t)|E(t)|^{2\gamma} \approx E(T)|E(T)|^{2\gamma}$ for $\chi > 0$, and introduce corresponding simplifying constants $k_{2\gamma+1}^\chi$, propagation equation becomes $$\partial_\xi E(\xi, r, T) \approx \Bigg[ \quad (22)$$
$$-\frac{\alpha_0}{2} + \frac{i}{2k_0}\nabla_\perp^2 + i\frac{\omega_0^2}{2k_0 c_0^2}\sum_{\gamma=1}^{N_\chi} k_{2\gamma+1}^\chi \chi^{(2\gamma+1)}|E|^{2\gamma} \Bigg] E(\xi, r, T),$$

where $k_3^\chi = 3$, $k_5^\chi = 0$, etc.

The following is a mathematical model which contains the resulting propagation equation coupled with a time-resolved (dimensionless) rate equation for a sample of a homogenous material of length L:

$$\frac{\partial N(\eta, \rho, \tau)}{\partial \tau} = T_0 \left[ D_0 + \sum_{\alpha=1}^{N_A} \frac{D_\alpha I_0^\alpha}{\alpha \hbar \omega_0} \overline{Q}^\alpha(\eta, \rho, \tau) \right] N(\eta, \rho, \tau), \quad (23)$$

$$\frac{\partial Q(\eta, \rho, \tau)}{\partial \eta} = \quad (24)$$

$$\left\{ -L_{df} N \left[ \sum_{\beta=1}^{N_B} (\sigma_\beta \cdot N(\eta, \rho, \tau)) I_0^{\beta-1} \overline{Q}^{\beta-1}(\eta - \rho, \tau) \right] - \tilde{c} L_{df} \right.$$

$$+ \frac{i}{4} \nabla_\rho^2 \quad (25)$$

$$\left. + i \sum_{\gamma=1}^{N_\chi} p_{2\gamma+1} \overline{Q}^\gamma(\eta, \rho, \tau) \right\} Q(\eta, \rho, \tau), \quad (26)$$

Initial Values:

$$Q(\eta=0, \rho, \tau) = f(\rho, \tau),$$

$$N(\eta, \rho, \tau < \tau_{min}) = [1, 0, \ldots, 0]^T, \quad (27)$$

Boundary Conditions:

$$Q(\eta, \rho=\infty, \tau) = Q(\eta, \rho, \tau=\pm\infty) = 0 \quad (28)$$

Equation (23) is the rate equation that describes how the population density vector N of the energy levels changes with time.

The propagation equation (24)-(26) contains four terms: multi-photon absorption, linear absorption [both terms are in (24)], diffraction in term (25), and nonlinear Kerr effect and higher-order polarization effects in term (26). The initial values for the equations are given by equation (27). The following is more detailed description of functions, variables and constants used in Eqs. (23)-(28).

N is the normalized vectors of population densities to be sought; $N(\eta,\rho,\tau)$ is a dimensionless vector function of $\eta$, $\rho$ and $\tau$, which are the normalized depth, radius and time, respectively; $N=[N_0, N_1, \ldots, N_{s-1}]^T$ for a system with S electronic levels; the ground state is initialized with value one before the pulse propagation: $N_0(\eta,\rho,\tau<\tau_{min})=1$.

$\overline{Q} \equiv QQ^*$, $Q(\eta,\rho,\tau)$ is a complex normalized electromagnetic field to be sought and $$f(\rho,\tau) = e^{-(r')^2/2} e^{-(p')^2/2} \quad (29)$$

is the pulse shape for a Gaussian pulse.

The electric field is given by the following SVEA:

$$E(z,r,t)_z = Q_0'[Q(z,r,t)\exp(ik_0 z - i\omega_0 t) + c.c.]. \quad (30)$$

The three dimensionless variables are within the following ranges:
- $\eta \in [0 \ldots \eta_{max}]$, $\eta_{max} = L/L_{df}$, where L is the length of the sample;
- $\rho \in [0 \ldots \rho_{max}]$, $\rho_{max} = R_{max}/R_0$, where $R_{max}$ is the radial size of the grid used in our numerical algorithm;
- $\tau \in [-\tau_{max} \ldots \tau_{max}]$, $\tau_{max} = T_{max}/T_0$, where $T_{max}$ is the temporal size of the grid.

The transformation of the variables from the cylindrical system of coordinates (z,r,t) to the normalized coordinates is the following:

$$\eta = \xi/L_{df} = z/L_{df}, \rho = r/R_0, \tau = T/T_0 = (t - k_1 z)/T_0. \quad (31)$$

$T_0, R_0$ are 1/e pulse temporal and radial half-width, respectively.

$L_{df} = \pi R_0^2 n_0/\lambda_0$ is the diffraction length when a pulse with wavelength $\lambda_0$ propagates through a material with linear index of refraction $n_0$.

$I_0 = 2\epsilon_0 n c_0 Q_0^{2'}$ is the absolute value of peak intensity of incident pulse; $I_0$ may be represented as a function of input parameters $E_{in}, R_0, T_0$, i.e., $I_0 = g_1(E_{in}, R_0, T_0)$, where $E_{in}$ is the incident input energy; for example, for a Gaussian pulse $$g_1(E_{in}, R_0, T_0) = E_{in}/\pi\sqrt{\pi} R_0^2 T_0. \quad (32)$$

N is the absolute value of molecular concentration in a given homogeneous material sample.

$D_0 = D_0(\{k_{s_2 s_1}\})$ is a constant S×S matrix of decay rate parameters $k_{s_2 s_1}$ between states $s_1$ and $s_2$.

$D_1 = D_1(\{\sigma_{s_1 s_2}\})$ is a constant S×S matrix of molar single-photon-absorption (SPA) cross-section parameters $\sigma_{s_1 s_2}$ between states $s_1$ and $s_2$.

$D_\alpha = D_\alpha(\{\sigma_{\alpha PA}\})$ is a constant S×S matrix of molar multi-photon-absorption (MPA) cross-section parameters $\sigma_{\alpha PA}$ when $\alpha > 1$ photons are absorbed; in this model we restrict $\alpha$ to be in $1 \leq \alpha \leq 3$.

$\sigma_1 \equiv \sigma_1(\{\sigma_{s_1 s_2}\})$, $\sigma_2 \equiv \sigma_2(\sigma_{TPA})$, $\sigma_3 \equiv \sigma_3(\sigma_{3PA})$, ..., $\sigma_{N_B} \equiv \sigma_{N_B}(\sigma_{N_B PA})$ are $N_B$ constant (mostly sparse) S dimensional vectors composed of certain elements of corresponding $D_\beta$ matrices (see detailed description below).

$\tilde{c}$ is the linear absorption coefficient.

$$p_{2\gamma+1} = \frac{\omega_0^2}{2k_0 c_0^2} k_{2\gamma+1}^\chi \chi_1^{(2\gamma+1)} (Q_0')^{2\gamma} L_{df}.$$

$\omega_0$ is the central frequency of incident pulse; $k_0$ is the wave number.

$\chi_1^{(2\gamma+1)}$ is the real part of susceptibility $\chi^{(2\gamma+1)}$ of the order $2\gamma+1$. $\chi_1^{(2\gamma+1)}$ are proportional to the corresponding terms of the nonlinear index of refraction for the material that is given by $$\tilde{n} = n_0 + n_2^1 I + n_4^1 I^2 + \quad (33)$$

The methods, systems and software arrangements of this invention provide user-interactive, computer-based processes and GUIs for generating the mathematical matrices and vectors needed to solve equations (23)-(28). The process of building the matrices $D_\alpha$ and vectors $\sigma_\beta$ is iterative. It starts from zero S×S matrices $D_\alpha=0$ and S-vectors $\sigma_\beta=0$, and adds corresponding terms (parameters) to the matrices $D_\alpha$ and vectors $\sigma_\beta$ for every transition within the energy level diagram of the material under investigation. For example, if there is a single photon absorption from level $s_1$ to level $s_2$, then the following update of the matrix $D_1$ and update of the vector $\sigma_1$ is performed: (Note that the update is done by adding or subtracting the absorption cross-section parameter $\sigma_{s_1 s_2}$ to the appropriate matrix or vector)

$$D_1[s_1, s_2] = D_1[s_1, s_2] - \sigma_{s_1 s_2},$$

$$D_1[s_2, s_1] = D_1[s_2, s_1] + \sigma_{s_1 s_2},$$

$$\sigma_1[s_1] = \sigma_1[s_1] + \sigma_{s_1 s_2}. \quad (34)$$

For an MPA transition with absorbing $\alpha$ photons, the update is done by adding or subtracting the absorption cross-section parameter $\sigma_{[\alpha]PA}$:

$$D_\alpha[s_1, s_2] = D_\alpha[s_1, s_2] - \sigma_{[\alpha]PA},$$

$$D_\alpha[s_2, s_1] = D_\alpha[s_2, s_1] + \sigma_{[\alpha]PA},$$

$$\sigma_\alpha[s_1] = \sigma_\alpha[s_1] + \sigma_{[\alpha]PA}. \quad (35)$$

For a relaxation transition from level $s_2$ to level $s_1$ we update only matrix $D_0$ by adding or subtracting the decay rate parameter $k_{s_2 s_1}$:$D_0$ $$D_0[s_2, s_1] = D_0[s_2, s_1] - k_{s_2 s_1},$$

$$D_0[s_1, s_2] = D_0[s_1, s_2] + k_{s_2 s_1}. \quad (36)$$

Figure 2:
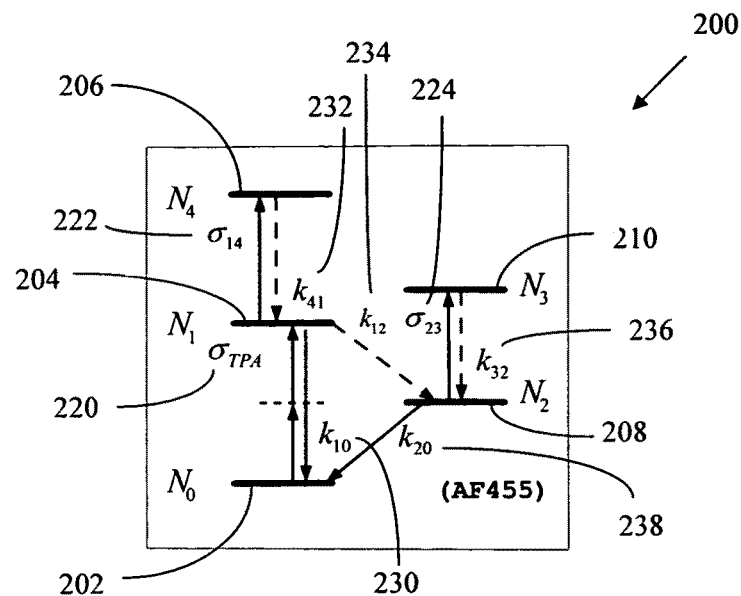
FIG. 2 is an energy level diagram for a chromophore AF455 that can undergo two-photon absorption (TPA). The absorption cross-section parameters and the relaxation rate parameters are indicated in the figure.

The following are the corresponding matrices and vectors used for simulating the transmittance of chromophore molecule AF455 whose 5-level energy level diagram with cross-section parameters and decay rate parameters is depicted in FIG. 2 as energy level diagram 200. Energy level diagram 200 has a ground singlet state 202 with electron population density $N_0$, excited singlet state 204 with electron population density $N_1$, excited singlet state 206 with electron population density $N_4$, lower triplet state 208 with electron population density $N_2$, and excited triplet state 210 with electron population density $N_3$.

The interaction of high intensity light with material AF455 can result in several types of electronic transitions. The interaction of high intensity light with electrons in the ground state 202 can promote the electrons to excited state 204. The interaction can occur by two-photon absorption with absorption cross-section parameter 220 ($\sigma_{TPA}$). Furthermore, high intensity light can promote electrons in excited state 204 to excited state 206 via single photon absorption with absorption cross-section parameter 222 ($\sigma_{14}$). Electrons in state 206 can relax to state 204 with decay rate parameter 232 ($k_{41}$). Electrons in state 204 can relax to ground state 202 at rate 230 ($k_{10}$) or relax to triplet state 208 with decay rate parameter 234 ($k_{12}$). Light can excite electrons in triplet state 208 to triplet excited state 210 via single-photon absorption with cross-section parameter 224 ($\sigma_{23}$). Electrons in triplet excited state 210 can relax to state 208 with decay rate parameter 236 ($k_{32}$). Electrons in triplet state 208 can relax to the singlet ground state 202 with decay rate parameter 238 ($k_{20}$).

The corresponding matrices and vectors in equations (23)-(27) that correspond to the molecule illustrated in FIG. 2 are given by:

$$D_0 = \begin{pmatrix} 0 & k_{10} & k_{20} & 0 & 0 \\ 0 & -(k_{10}+k_{12}) & 0 & 0 & k_{41} \\ 0 & k_{12} & -k_{20} & k_{32} & 0 \\ 0 & 0 & 0 & -k_{32} & 0 \\ 0 & 0 & 0 & 0 & -k_{41} \end{pmatrix}, \quad (37)$$

$$D_1 = \begin{pmatrix} 0 & 0 & 0 & 0 & 0 \\ 0 & -\sigma_{14} & 0 & 0 & 0 \\ 0 & 0 & -\sigma_{23} & 0 & 0 \\ 0 & 0 & \sigma_{23} & 0 & 0 \\ 0 & \sigma_{14} & 0 & 0 & 0 \end{pmatrix}, \quad D_2 = \begin{pmatrix} -\sigma_{TPA} & 0 & 0 & 0 & 0 \\ \sigma_{TPA} & 0 & 0 & 0 & 0 \\ 0 & 0 & 0 & 0 & 0 \\ 0 & 0 & 0 & 0 & 0 \\ 0 & 0 & 0 & 0 & 0 \end{pmatrix}, \quad (38)$$

$$\sigma_1 = [0, \sigma_{14}, \sigma_{23}, 0, 0], \quad \sigma_2 = [\sigma_{TPA}, 0, 0, 0, 0]. \quad (39)$$

In the case of AF455, $N_A = N_B = 2$, where $N_A$ and $N_B$ are the summation indices in Eq. (8) and Eq. (9), respectively. AF455 has five energy levels (S=5).

Figure 3:
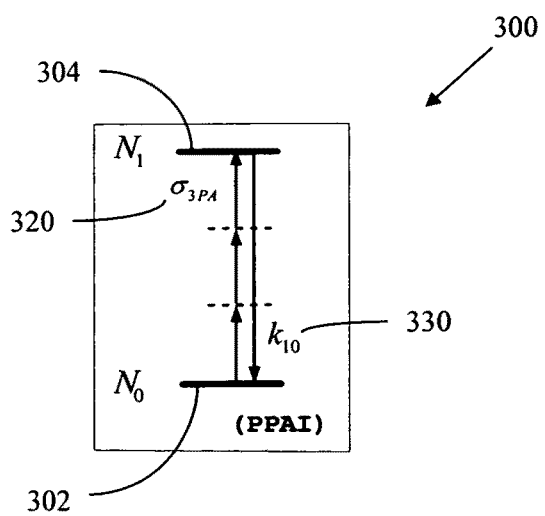
FIG. 3 is an energy level diagram for a dye molecule PPAI that can undergo three-photon absorption (3PA). The 3PA absorption cross-section parameter and the relaxation rate parameter are indicated in the figure.

The following is another simple example of constructing the corresponding matrices and vectors for a three-photon absorbing (3PA) dye, abbreviated as PPAI. The energy level diagram 300 for PPAI is illustrated in FIG. 3. For PPAI, $N_A = N_B = 3$, S=2. PPAI has two states, ground state 302 with electron population density $N_0$ and excited state 304 with electron population density $N_1$. Electrons in the ground state 302 of PPAI can be excited to excited state 304 via three-photon absorption with absorption cross-section parameter 320 ($\sigma_{3PA}$). Electrons in the excited state 304 can relax to the ground state 302 with decay rate parameter 330 ($k_{10}$).

$$D_0 = \begin{pmatrix} 0 & k_{10} \\ 0 & -k_{10} \end{pmatrix}, \quad D_1 = D_2 = 0, \quad D_3 = \begin{pmatrix} -\sigma_{3PA} & 0 \\ \sigma_{3PA} & 0 \end{pmatrix} \quad (40)$$

$$\sigma_1 = \sigma_2 = 0, \quad \sigma_3 = [\sigma_{3PA}, 0]. \quad (41)$$

The following are examples of two types of pulses that can be utilized: (1) a Gaussian pulse, which has a Gaussian shape in both radial and time domains, and (2) Gaussian-HSecantSq (hyperbolic-secant-squared) pulse, which is Gaussian in radial domain and has a hyperbolic secant squared shape in time domain. The following is a summary of functional representation of these pulses with their parameters. Pulse parameters $I_0, R_0, T_0$ are given as functions of incident intensity $E_{in}$, full width at half maximum $t_{FWHM}$ (defined in terms of the pulse power), and $1/e^2$ radius of the beam $w_{HW1/e^2M}$ (defined in terms of beam intensity).

For a Gaussian pulse:

$$f(\rho, \tau) = e^{-\rho^2/2} e^{-\tau^2/2} + 0i \quad (42)$$

$$I(\eta = 0, \rho, \tau) = I_0 e^{-\rho^2} e^{-\tau^2}$$

$$T_0 = t_{FWHM}/2\sqrt{\ln 2}$$

$$R_0 = w_{HW1/e^2M}/\sqrt{2}$$

$$I_0 \approx \frac{E_{in}}{\pi\sqrt{\pi} R_0^2 T_0}$$

For a Gaussian-HSecantSq pulse:

$$f(\rho, \tau) = e^{-\rho^2/2} \text{sech}(\tau) + 0i \quad (43)$$

$$I(\eta = 0, \rho, \tau) = I_0 e^{-\rho^2} \text{sech}^2(\tau)$$

$$T_0 = t_{FWHM}/2\ln(1 + \sqrt{2})$$

$$R_0 = w_{HW1/e^2M}/\sqrt{2}$$

$$I_0 \approx \frac{E_{in}}{2\pi R_0^2 T_0}$$

For a layered material with $N_L$ layers, one can write $N_L$ copies of equations (23)-(26), one copy for each layer, and use the solution of the equations (23)-(27) for each such layer as the initial condition in equation (27) for the next layer. Solving sequentially the equations for all the layers, gives a resulting electromagnetic field at the exit surface of the last layer.

The solution of the partial differential equations uses a variant of a finite difference split-step method enhanced by Crank-Nicholson numerical scheme. The following is a short description of the method. If the original system of coupled equations (23)-(26) is written in the following operator form:

$$\frac{dN(\eta, \rho, \tau)}{d\tau} = \Upsilon_{rate}(\eta, \rho, \tau) \cdot N(\eta, \rho, \tau), \quad (44)$$

$$\frac{dQ(\eta, \rho, \tau)}{d\eta} = \begin{bmatrix} \Phi_{rate}(\eta, \rho, \tau) + \\ \Psi_{df}(\eta, \rho, \tau) + \Psi_K(\eta, \rho, \tau) \end{bmatrix} \cdot Q(\eta, \rho, \tau), \quad (45)$$

where

-continued $$\Upsilon_{rate}(\eta, \rho, \tau) = T_0 \left[ D_0 + \sum_{\alpha=1}^{N_A} \frac{D_\alpha I_0^\alpha}{\alpha \hbar \omega_0} \overline{Q}^\alpha(\eta, \rho, \tau) \right] \quad (46)$$

$$\equiv \Upsilon_0 + \sum_{\alpha=1}^{N_A} \Upsilon_\alpha^Q(\eta, \rho, \tau),$$

$$\Phi_{rate}(\eta, \rho, \tau) = -L_{df} N \left[ \sum_{\beta=1}^{N_B} (\sigma_\beta \cdot N(\eta, \rho, \tau)) I_0^{\beta-1} \overline{Q}^{\beta-1}(\eta, \rho, \tau) \right] - \tilde{c} L_{df} \quad (47)$$

$$\equiv \sum_{\beta=1}^{N_B} \Phi_\beta^N(\eta, \rho, \tau) \Phi_\beta^Q(\eta, \rho, \tau) + \Phi_c,$$

$$\Psi_{df}(\eta, \rho, \tau) = \frac{i}{4} \nabla_\rho^2 \Big|_{(\eta, \rho, \tau)}, \quad (48)$$

$$\Psi_K(\eta, \rho, \tau) = i \sum_{\gamma=1}^{N_K} p_{2\gamma+1} \overline{Q}^\gamma(\eta, \rho, \tau). \quad (49)$$

Then an approximate solution of the propagation equation from propagation distance $\eta$ to $\eta + \Delta\eta$ may be described by the following split-step method integration scheme $$N(\tau + \Delta\tau) \approx \exp\left( \int_\tau^{\tau+\Delta\tau} \Upsilon_{rate}(\eta', \rho, \tau') d\tau' \right) \cdot N(\tau). \quad (50)$$

$$Q(\eta + \Delta\eta) \approx e^{\frac{\Delta\eta}{2} \Psi_{df}(\rho, \tau)} \cdot \quad (51)$$

$$\exp\left( \int_\eta^{\eta+\Delta\eta} \Phi_{rate}(\eta', \rho, \tau) + \Psi_K(\eta', \rho, \tau) d\eta' \right) \cdot e^{\frac{\Delta\eta}{2} \Psi_{df}(\rho, \tau)} \cdot Q(\eta),$$

A pulse propagates within the following 3-dimensional (depth×time×radial) domain $D_{\eta\rho\tau} = D_\eta \times D_\rho \times D_\tau$:

$$D_\eta = [0 \ldots \eta_{max}] \quad (52)$$

$$D_\rho = [0 \ldots \rho_{max}] \quad (53)$$

$$D_\tau = [-\tau_{max} \ldots \tau_{max}] \quad (54)$$

The domain $D_{\eta\rho\tau}$ is given in normalized coordinates $(\eta, \rho, \tau)$, while its real counterpart $D_{zrt} = D_z \times D_r \times D_t$, written in a cylindrical coordinates $(z, r, t)$, is defined by $$D_z = [0 \ldots L], D_r = [0 \ldots R_{max}], D_t = [-T_{max} \ldots T_{max}] \quad (55)$$

Two different 3D grids are used to discretize the domain D: one grid $\Omega_N$ is for the rate equation (50) and the other grid $\Omega_Q$ is for the propagation equation (51). Therefore, the entire grid is a pair $\Omega = \{\Omega_Q, \Omega_N\}$ The grids definitions are $$\rho_j = \rho_0 + j\Delta\rho, \quad (56)$$

$$\Omega_Q = \{(\eta_n, \rho_j, \tau_i) : n=0 \ldots N_\eta-1, j=0 \ldots N_\rho-1, i=1-N_\tau \ldots N_\tau-1\}, \quad (57)$$

$$\eta_n = \eta_0 + n\Delta\eta, \tau_i = \tau_0 + i\Delta\tau; \quad (58)$$

$$\Omega_N = \{(\eta_{n+1/2}, \rho_j, \tau_{i+1/2}) : n=0 \ldots N_\eta-1, j=0 \ldots N_\rho-1, i=1-N_\tau \ldots N_\tau-1\}, \quad (59)$$

$$\eta_{n+1/2} = (\eta_0 + \Delta\eta/2) + n\Delta\eta, \tau_{i+1/2} = (\tau_0 + \Delta\tau/2) + i\Delta\tau. \quad (60)$$

Figure 4:
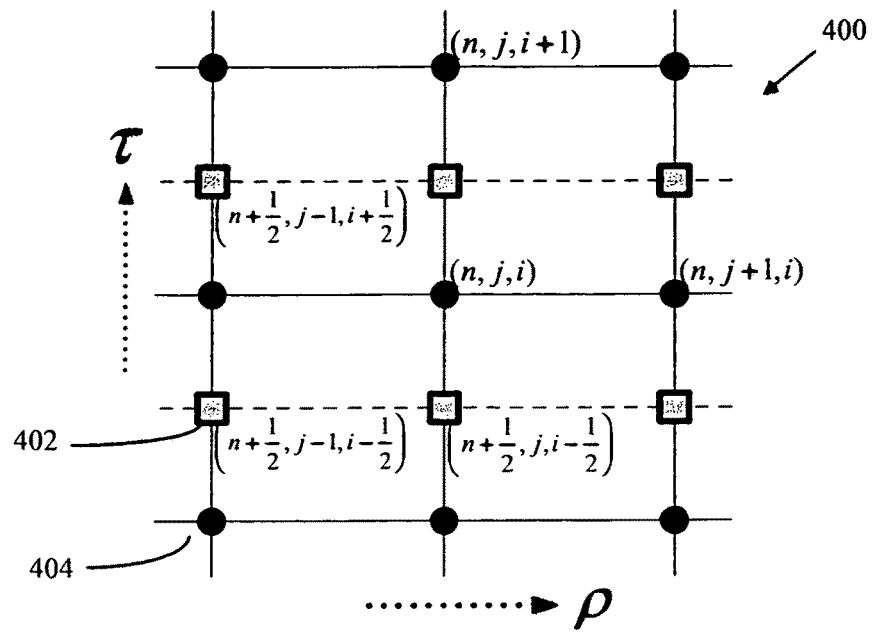
FIG. 4 is a plan view of the superimposed numerical grids $\Omega_Q$ (circular grid points) for calculating the propagation of the electric field and $\Omega_N$ (square grid points) for calculating electronic population densities. The superimposed grids are viewed along depth η-axis at depths $\eta=\eta_n$ (for the electric field) and $\eta=\eta_n+\Delta\eta/2$ (for the electronic population density).
Figure 5:
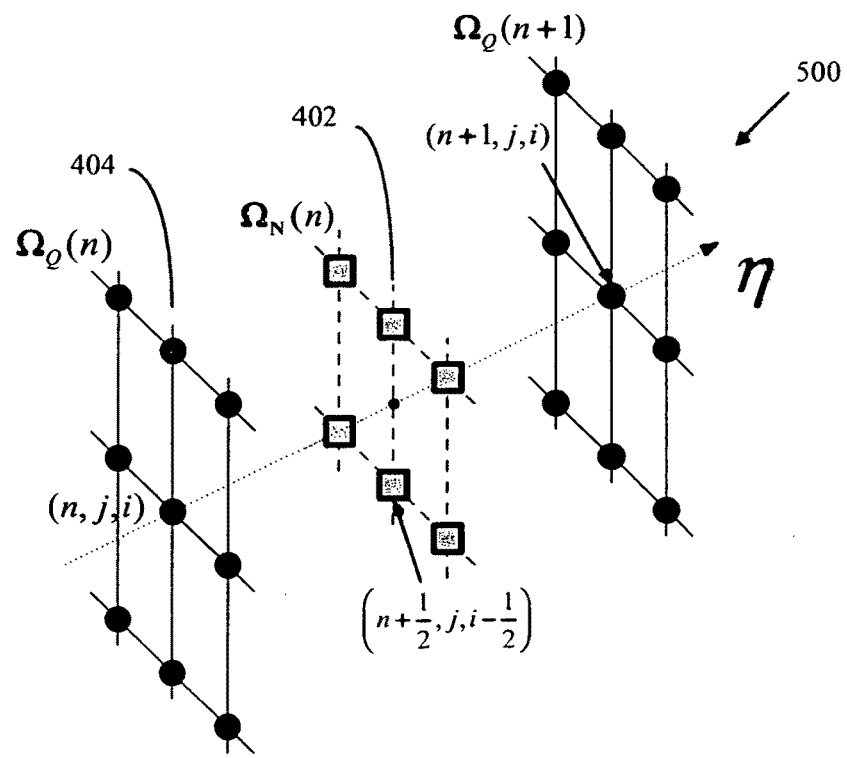
FIG. 5 illustrates a three-dimensional perspective view of the relative positions of the propagation equation grid fragments $\Omega_Q(n)$ and $\Omega_Q(n+1)$ (circular grid points) and the rate equation grid fragment $\Omega_N(n)$ (square grid points).

The samples of these two grids coincide along the radial domain (shown in a cross-sectional plan view in FIG. 4), and interleave along depth and time (shown in a three-dimensional perspective view in FIG. 5). The interleaving of the two grids will guarantee better convergence. In FIGS. 4 and 5, the grid 402 for calculating electronic population densities is denoted by the square grid points. The grid 404 for calculating the propagation of the electric field is denoted by circular grid points. To save space, the index ranges are labeled as follows $$J_\eta = 0 \ldots N_\eta - 1, \quad (61)$$

$$J_\rho = 0 \ldots N_\rho - 1, \quad (62)$$

$$J_\tau = 1 - N_\tau \ldots N_\tau - 1. \quad (63)$$

One can think of $\Omega_Q$ and $\Omega_N$ as two families of 2-dimensional grids indexed by the depth samples: $\Omega_Q = \{\Omega_Q(n)\}_{n \in J_\eta}$ and $\Omega_N = \{\Omega_N(n)\}_{n \in J_\eta}$, respectively. The relative positions of neighboring snapshots $\Omega_Q(n)$, $\Omega_N(n)$, and $\Omega_Q(n+1)$ at depth samples $\eta_n, \eta_{n+1/2}$, and $\eta_{n+1}$, correspondingly, are shown in FIG. 5. Again, grid 402 for calculating electronic population densities is denoted by the square grid points and the grid 404 for calculating the propagation of the electric field is denoted by circular grid points. In this document we denote grid values of the electromagnetic field (EMF) and the population density by either $Q_{n,j,i}$ and $N_{n+1/2,j,i+1/2}$, or by Q[n,j,i] and N[n+1/2,j,i+1/2], respectively:

$$Q_{n,j,i} \equiv Q(\eta_n, \rho_j, \tau_i), \quad (64)$$

$$N_{n+1/2,j,i+1/2} \equiv N(\eta_{n+1/2}, \rho_j, \tau_{i+1/2}). \quad (65)$$

It is straightforward to write discrete versions of the operators—defined on the grid $\Omega$; we denote them as follows: $\hat{\Upsilon}_{rate}[n,j,i] = \Upsilon_{rate}(\eta_n, \rho_j, \tau_i)$, $\hat{\Upsilon}_\alpha^Q[n,j,i] = \Upsilon_\alpha^Q(\eta_n, \rho_j, \tau_i)$, $\hat{\Phi}_\beta^N[n,j,i] = \Phi_\beta^N(\eta_n, \rho_j, \tau_i)$, $\hat{\Phi}_\beta^Q[n,j,i] \hat{\Phi}_\beta^Q(\eta_n, \rho_j, \tau_i)$, $\hat{\Psi}_{df}[n,j,i] = \Psi_{df}(\eta_n, \rho_j, \tau_i)$, $\hat{\Psi}_K[n,j,i] = \Psi_K(\eta_n, \rho_j, \tau_i)$. We apply a variant of Crank-Nicholson method to Eqs (50) and (51) and run K iterations till it converges to a solution for a given depth sample $\eta_{n+1}$. The following is the iteration scheme at $\eta_{n+1}$ showing a solution improvement during k-th iteration, k= 1, . . . , K, where K may be a small positive integer:

$$N_{n+1/2,j,i+1/2}^{(k)} =$$

$$\exp\left( \Delta\tau \Upsilon_0 + \sum_{\alpha=1}^{N_A} \frac{\Delta\tau}{2} \{\hat{\Upsilon}_\alpha^Q[n] + \hat{\Upsilon}_\alpha^{Q(k)}[n+1]\} \right) N_{n+1/2,j,i-1/2}^{(k)}, \quad (66)$$

$$Q_{n+1,j,i}^{(k+1)} = \exp\left( \frac{\Delta\eta}{4} \{\hat{\Psi}_{df}[n] + \hat{\Psi}_{df}^{(k)}[n+1]\} \right) \quad (67)$$

$$\cdot \exp(\Delta\eta \Phi_c) \quad (68)$$

$$\times \exp\left( \sum_{\beta=1}^{N_B} \frac{\Delta\eta}{4} \left\{ \hat{\Phi}_\beta^N \left[ n+\frac{1}{2}, j, i-\frac{1}{2} \right] + \hat{\Phi}_\beta^N \left[ n+\frac{1}{2}, j, i+\frac{1}{2} \right] \right\} \right) \quad (69)$$

$$\times \frac{1}{2} \times \{\hat{\Phi}_\beta^Q[n] + \hat{\Phi}_\beta^{Q(k)}[n+1]\} \quad (70)$$

$$\times \exp\left( \frac{\Delta\eta}{2} \{\hat{\Psi}_K[n] + \hat{\Psi}_K^{(k)}[n+1]\} \right) \quad (71)$$

$$\times \exp\left( \frac{\Delta\eta}{4} \{\hat{\Psi}_{df}[n] + \hat{\Psi}_{df}^{(k)}[n+1]\} \right) \cdot Q_{n,j,i}^{(k)}. \quad (72)$$

As a result of the calculations summarized above, one can determine, for example, the populations of the various energy levels in the material and the transmission or absorption of the electromagnetic radiation in the material. By analyzing radiation relaxation processes, one can also determine the amount of light emission from the material due to radiative relaxation.

One embodiment of this invention is a computer-based method that uses an application program and a graphical user interface to simulate and analyze an interaction between electromagnetic radiation and a material. The method is illustrated schematically by the flow diagram 600 in FIG. 6A.

Electromagnetic radiation includes, but is not limited to, visible light, ultraviolet light, infrared light, x-rays and microwaves. Materials include, for example, organic, inorganic, crystalline, amorphous, layered or composite materials. The material may have single layer or composition or the material may have two or more different layers or the material may have at least one layer that includes at least two different compositions.

Figure 6A:
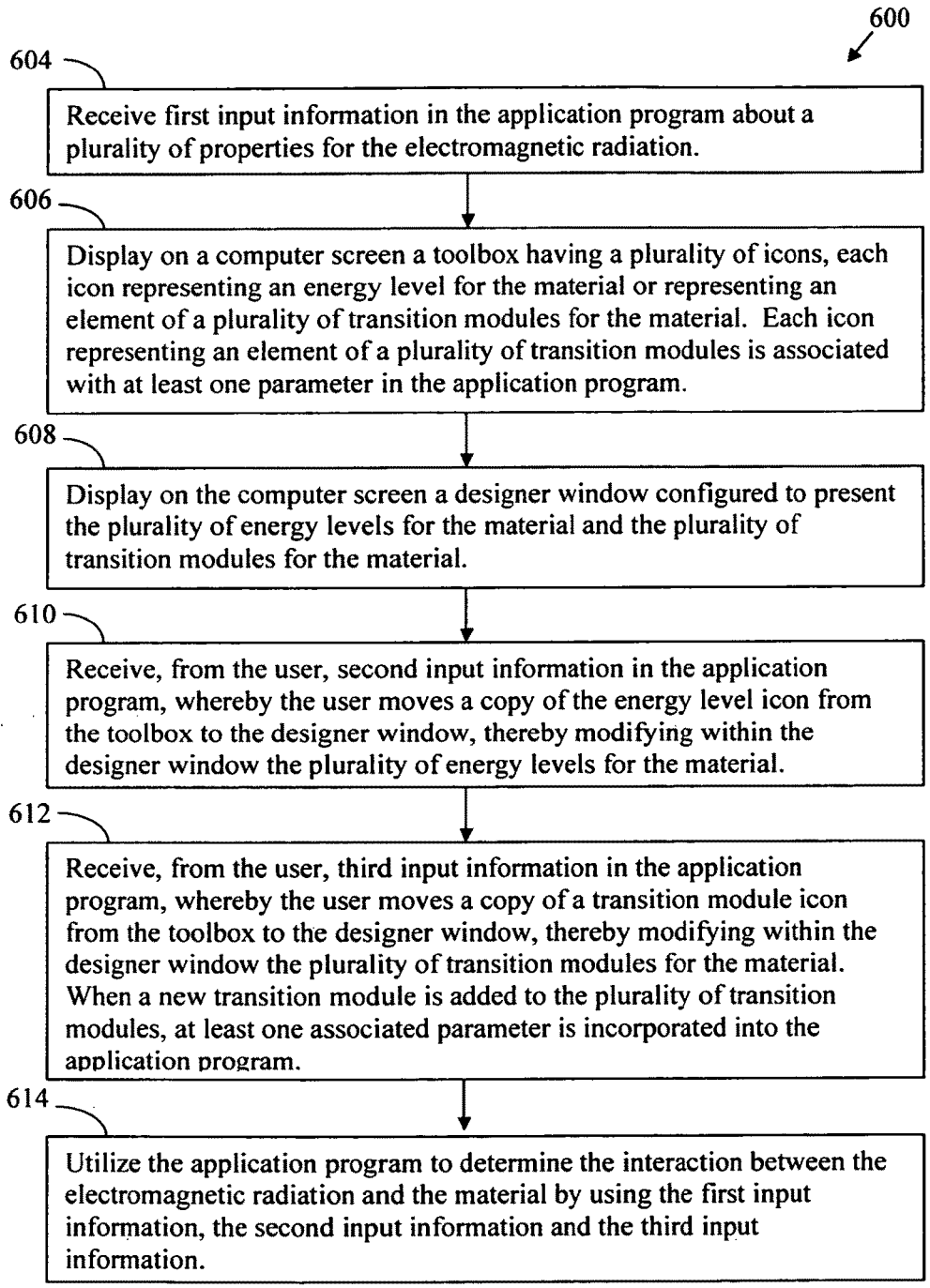
FIG. 6A is a flow diagram for a method embodiment of this invention.

The flow diagram in FIG. 6A lists a series of steps. However, the steps in the flow diagram 600 do not need to be done in the order listed. For example, the order of providing the first input information and the second input information may be reversed.

Step 604 of this method is for a user to provide first input information to the application program about a plurality of properties for the electromagnetic radiation. The first information can include, but is not limited to, the direction, the duration, the magnitude of the electric field as a function of the radial profile, the intensity of the electric field as a function of the radial profile and the wavelength of the electromagnetic radiation.

Step 606 of this embodiment is to display on a computer screen a toolbox having a plurality of icons. Each icon represents either an energy level for the material or an element of a plurality of transition modules for the material. If the icon represents an element of a plurality of transition modules, the icon is also associated with at least one parameter in the application program. The transition module icons can include an absorption transition module icon, a relaxation transition module icon, an electron transfer transition module icon, an energy transfer transition module icon and an up-conversion transition module icon.

Step 608 of this method is to display a designer window on the computer screen. The designer window is configured to present the plurality of energy levels for the material and the plurality of transition modules in for the material. If the material has two or more differing components, layers or compositions, two or more sets of energy levels and two or more sets of transition modules can be presented in one or more designer windows.

In step 610, the user provides second input information to the application program. The user moves a copy of the energy level icon from the toolbox to the designer window, thereby modifying in the designer window the plurality of energy levels for the material. This change in the position of the energy level icon is detected by the computer, and the second input information is thereby received by the application program In step 612, the user provides a third input information to the application program. The user moves a copy of a transition module icon from the toolbox to the designer window, thereby modifying within the designer window the plurality of transition modules for the material. This change in the position of the icon is detected by the computer, and third input information is thereby received by the application program. In addition, if a new transition module is added to the plurality of transition modules, then at least one associated parameter is incorporated into the application program. For example, these parameters may be entered by the user into the application program in response to prompts issued by the application program.

In step 614 following the additions of the first input, the second input and the third input, the application program determines the interaction between the electromagnetic radiation and the material using the provided information. Calculating the interaction can include, for example, determining the electronic population for at least one of the plurality of energy levels and/or determining, for example, a transmission factor, an absorption factor or an emission factor for the electromagnetic radiation in the material.

For example, if a laser pulse is directed to a material and is partially transmitted by the material, the transmission factor, $T_E$, is given by the pulse energy, $E_{out}$, which exits the material divided by the pulse energy, $E_{in}$, that enters the material. The transmission factor, $T_E$, can be calculated by equation (73) below.

$$T_E = \frac{E_{out}(\eta_{max})}{E_{in}(0)} = \frac{\int_0^{+\infty} dr' 2\pi r' \int_{-\infty}^{+\infty} dt' I(r', t', \eta_{max})}{\int_0^{+\infty} dr' 2\pi r' \int_{-\infty}^{+\infty} dt' I(r', t', 0)} \quad (73)$$

In equation (73), the intensity I is proportional to the square of the electric field. For this example, the absorption factor, $A_E$, for the material is given by $1-T_E$. An emission factor for a material is, for example, the portion of the electronic population of an excited energy level that relaxes to a lower energy level by the emission of light or other electromagnetic radiation.

Figure 6B:
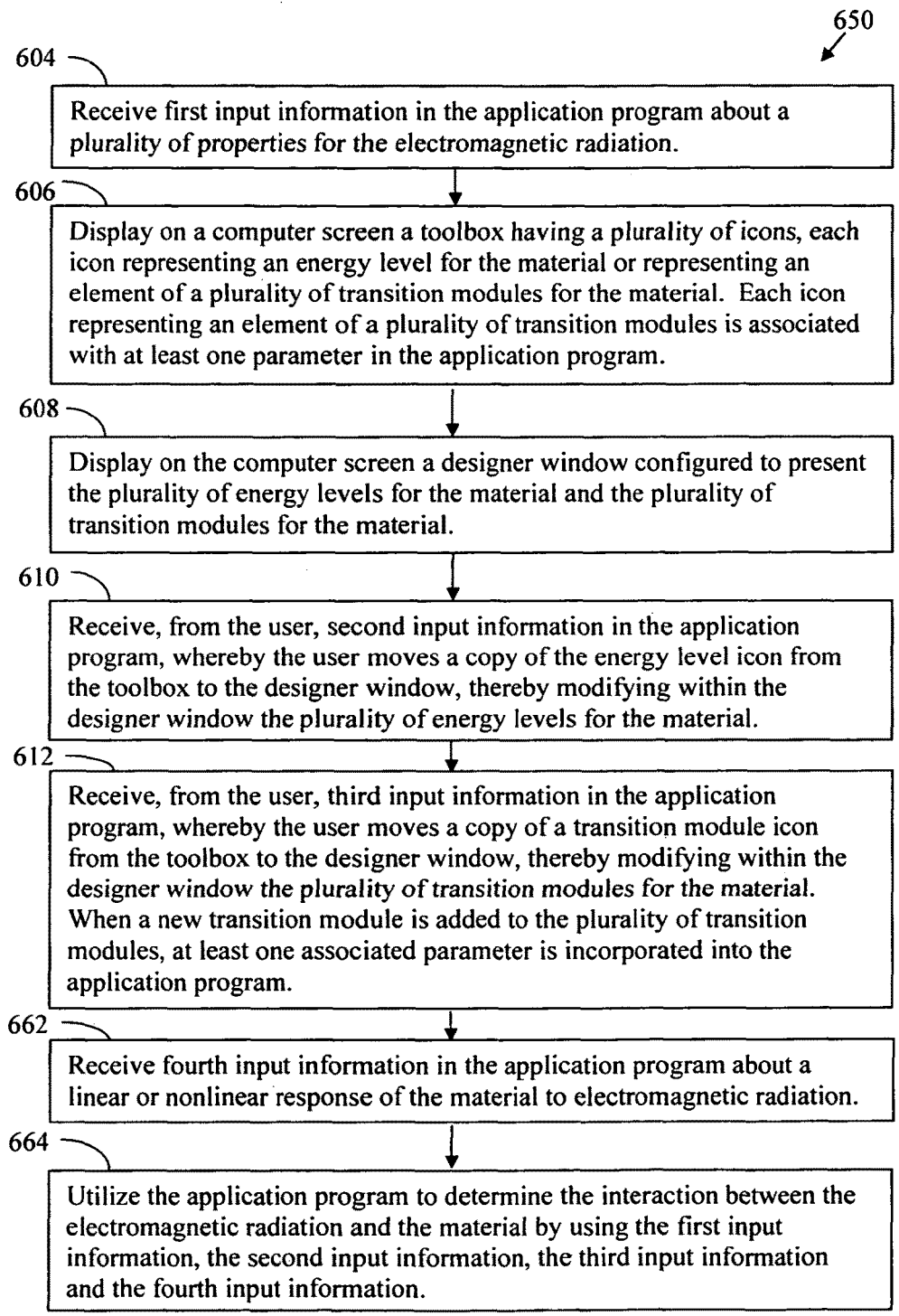
FIG. 6B is a flow diagram for another method embodiment.

A modified embodiment of this method is illustrated schematically as flow diagram 650 in FIG. 6B. Steps 604, 606, 608, 610 and 612 in flow diagram 650 are identical to the equivalent steps in FIG. 6A. However, in diagram 650, a user provides fourth information to the application program in step 662. The fourth information can include, for example, information about a linear or nonlinear response of the material to the electromagnetic radiation. In step 664, the application program then calculates the interaction of the electromagnetic radiation and the material using the first, second, third and fourth information. An example of a linear response is diffraction or linear dispersion. Examples of nonlinear responses include, but are not limited to, a Kerr effect, a nonlinear dispersion effect or a nonlinear index of refraction effect resulting from a $\text{Re}\chi^{(3)}$ effect, a $\text{Re}\chi^{(5)}$ effect or a $\text{Re}\chi^{(2n+1)}$ effect of higher order with n>1. The term $\text{Re}\chi^{(5)}$, for example, refers to the real part of the nonlinear susceptibility $\chi^{(5)}$ of order 5.

An illustrative example of the computer screen, toolbox and designer window associated with steps 606, 608 and 610 of flow diagrams 600 (FIG. 6A) and 650 (FIG. 6B) is shown schematically in FIGS. 7A-7E. This example is not meant to limit the scope of the invention. The details of the toolbox, the designer window and the associated steps to design the energy level diagram and energy level transitions may be different than the schematic illustrations in FIGS. 7A-7E. The computer screen, toolbox and designer window in FIGS. 7A-7E represent a schematic example of a graphical user interface of this invention.

Figure 7A:
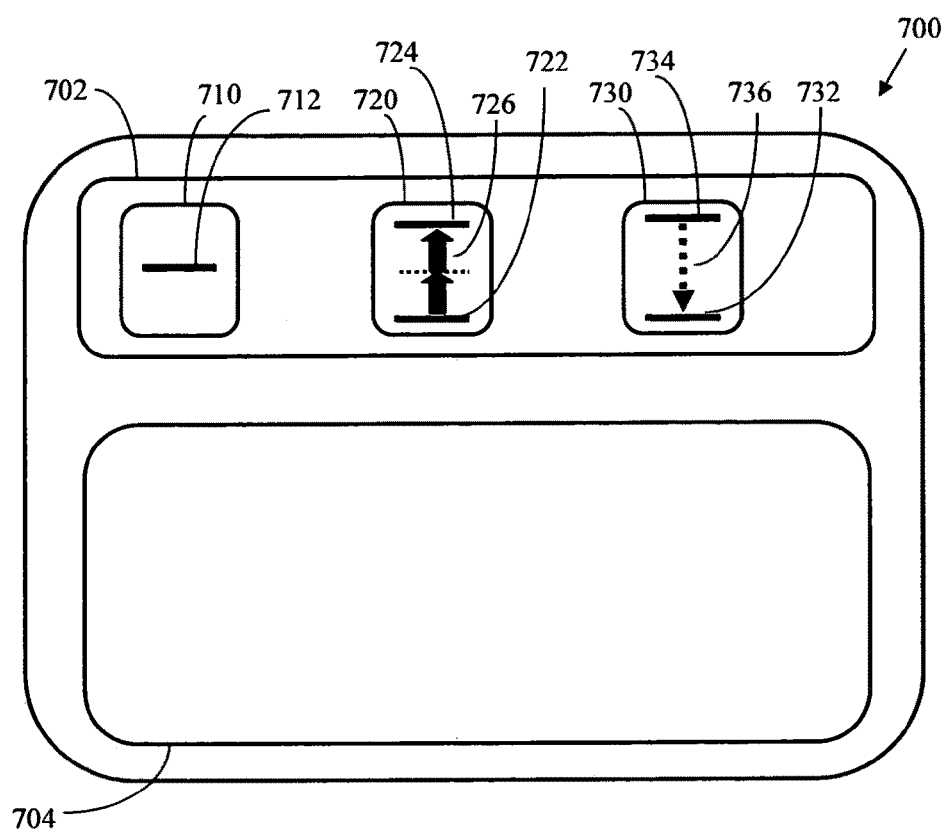
FIGS. 7A-7E illustrates views of a computer screen that show a toolbox and a designer window.

FIG. 7A illustrates an example of computer screen 700 that displays a toolbox 702 and a designer window 704. The toolbox contains a set of icons, three of which icons 710, 720 and 730 are depicted for illustrative purposes. It is also within the scope of this invention that the toolbox may contain more than three icons. In addition to the types of icons shown, the toolbox may also contain icons for an electron transfer transition module, an energy transfer transition module and an up-conversion transition module.

Icon 710 represents an energy level 712 for the material. Dragging a copy of icon 710 from the toolbox 702 to the designer window 704 will cause an energy level to be displayed in the designer window.

Icon 720 represents a type of transition module called an absorption transition module. An absorption transition module represents the absorption of light or other electromagnetic radiation by the material, resulting in an electron, for example, to be promoted from a lower energy state to a higher energy state. Dragging a copy of icon 720 from the toolbox to the designer window will cause an absorption transition to be displayed in the designer window and at least one corresponding parameter will be created or updated in the application program. For example, one such parameter for icon 720 is an absorption cross-section.

Icon 730 represents a type of transition module called a relaxation transition module. A relaxation transition module represents a relaxation process in the material, resulting in an electron, for example, relaxing from a higher energy level to a lower energy state. Dragging a copy of icon 730 from the toolbox to the designer window will cause a relaxation transition to be displayed in the designer window and at least one corresponding parameter will be created or updated in the application program. For example, one such parameter for icon 730 is a radiative or non-radiative decay rate.

The steps to utilize a computer-based GUI to design a two-level molecule that has an absorption process and a relaxation process will now be described. This process can be extended (not shown) to design molecules with an arbitrary number of energy levels and with an arbitrary number of transition processes. For example, the energy level diagram and transitions illustrated in FIG. 2 can be designed in the designer window. This process is a form of computer aided design (CAD) for material properties and will be denoted as M-CAD, which is an abbreviation for material computer aided design. The flexibility of the M-CAD process allows a computer user to design and subsequently simulate very complex molecules.

FIG. 7A illustrates the toolbox 702 and the designer window 704 before the start of the material design. The designer window is empty.

Figure 7B:
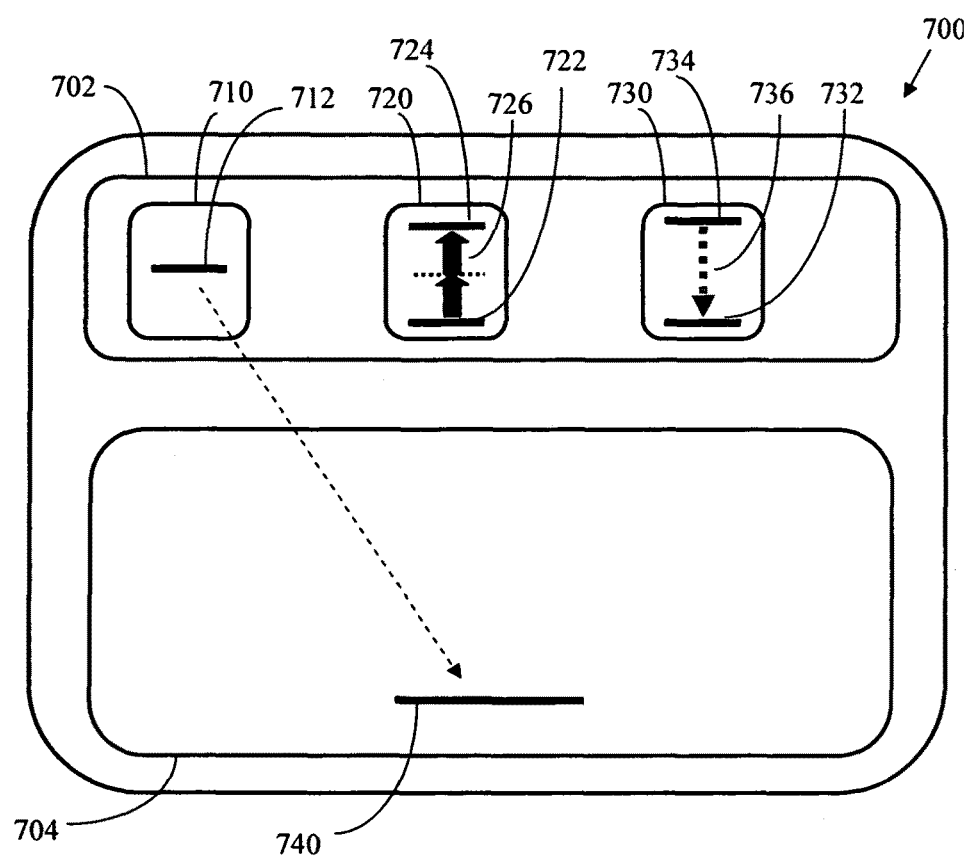

In FIG. 7B, a user drags a first copy of the energy level icon 710 into the designer window, causing a first energy level 740 to be displayed in the designer window. The user assigns a number, such as level 0, to the energy level. This level number, level 0, is part of the second input information that is transferred to the application program.

Figure 7C:
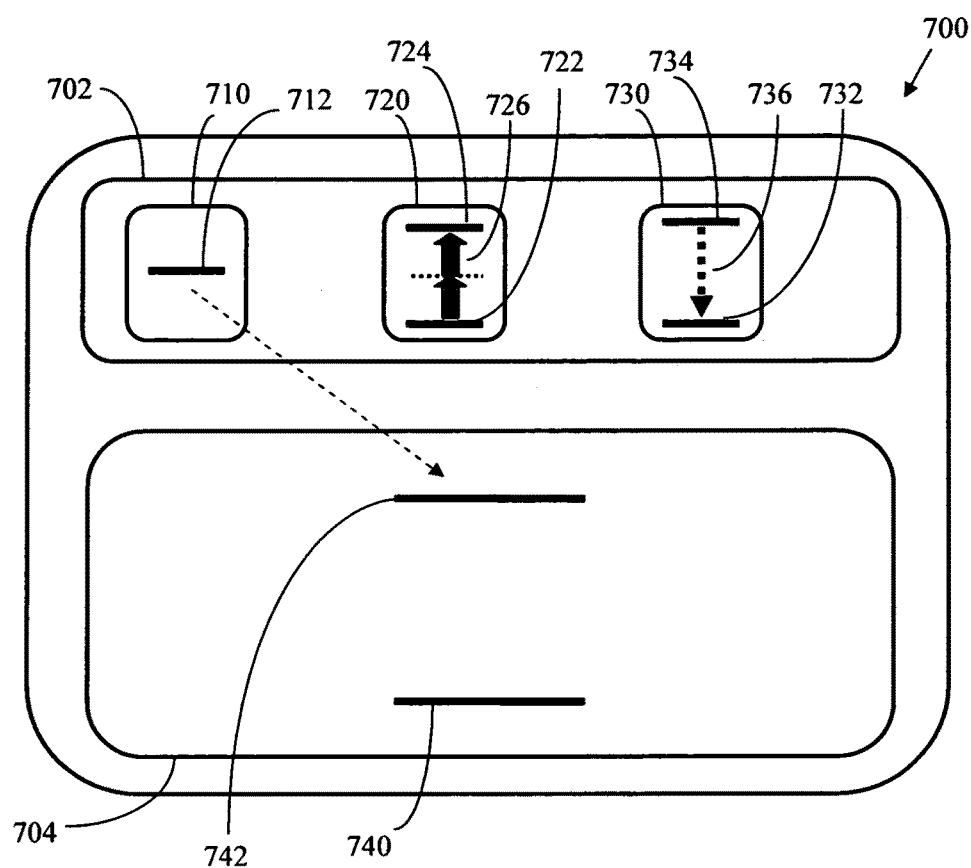

In FIG. 7C, a user drags a second copy of the energy level icon 710 into the designer window, causing a second energy level 742 to be displayed in the designer window. The user assigns a number, such as level 1, to the energy level. The level number, level 1, is another part of the second input information that is transferred to the application program. The total number of energy levels determines the size of the matrices and vectors in Eqs. (23) and (24). For example, if there are two energy levels the matrices are 2×2 matrices and the vectors each have two elements.

Figure 7D:
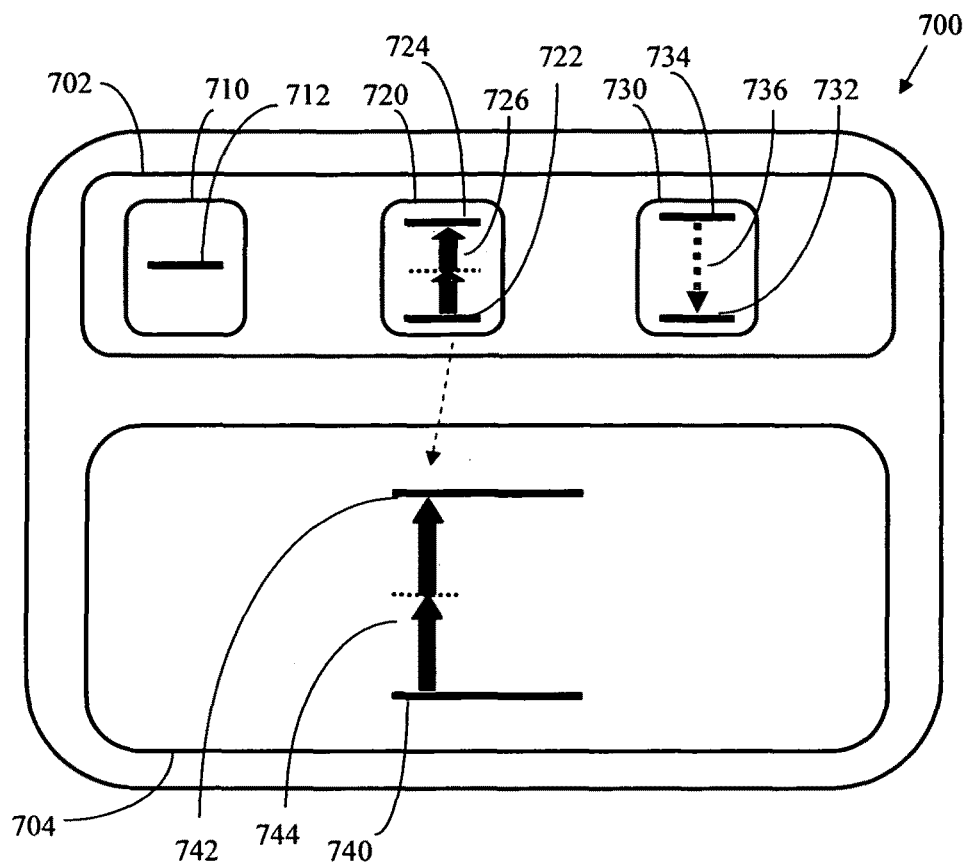

FIG. 7D illustrates a user dragging a copy of icon 720 into the designer window. The copy of icon 720 represents an absorption transition module 744 that is displayed in the designer window. The user connects the absorption transition module 744 to the energy levels 740 and 742. The absorption transition module can represent single-photon absorption (SPA), two-photon absorption (TPA) as illustrated in FIG. 7D, three-photon absorption (3PA), four-photon absorption (4PA) or any type of multi-photon absorption (MPA). The absorption module 744 is also associated with a spin manifold index parameter (such as singlet or triplet) and with an absorption cross-section parameter that determines the probability that one or more photons will be absorbed by an electron in energy level 740 and be promoted to energy level 742. In all, the absorption module is associated with at least five parameters, the starting energy level, the ending energy level, the number of photons involved (SPA, TPA, 3PA and so forth), the spin manifold index and the absorption cross-section. After the user drags a copy of icon 720 into the designer window, the user assigns values to the five parameters. The assigned values are transferred to the application program as part of the third input information. For example, SPA cross-section parameters will be added to the $D_1$ matrix that is incorporated into Eq. (23). TPA cross-section parameters will be added to the $D_2$ matrix that is incorporated into Eq. (23).

Figure 7E:
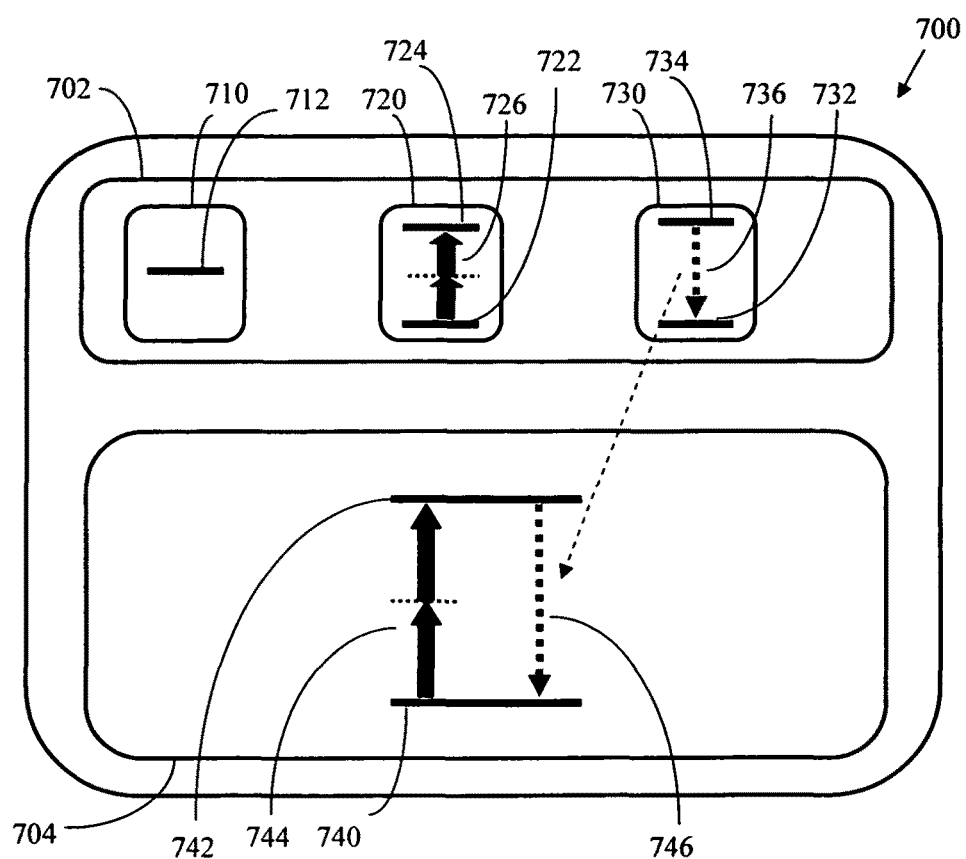

FIG. 7E illustrates a user dragging a copy of icon 730 into the designer window. The copy of icon 730 represents a relaxation transition module 746 that is displayed in the designer window. The user connects the relaxation transition module 746 to the energy levels 742 and 740. The relaxation transition module can represent radiative or non-radiative relaxation. The relaxation transition module 746 is also associated with a relaxation rate parameter that describes the speed or time for relaxation from energy level 742 to energy level 740. In all, the relaxation module is associated with at least six parameters, the starting energy level, the ending energy level, the relaxation type (radiative or non-radiative), the spin manifold index for the starting energy level, the spin manifold index for the ending energy level and the relaxation rate. When the user drags a copy of icon 730 into the designer window, the user also assigns values to the six parameters. The assigned values are transferred to the application program as part of the third input information.

To summarize, FIGS. 7A-7E describe a process that allows a computer user to utilize a GUI to design the optical properties of the material using a plurality of energy levels and a plurality of transition modules that represent electronic transitions. If the material is a layered material or a composite material that contains two or more different compositions, two or more diagrams may be needed to describe the energy levels and transition modules for the two compositions. The two or more diagrams may be constructed in one designer window or in multiple designer windows.

In FIGS. 7A-7E, only two types of transition icons or transition modules are illustrated. Several types of electronic transitions or transition modules are possible. The several types will be described below. First, the descriptions of the absorption transition module and the relaxation transition module will be repeated in greater detail.

Figure 8:
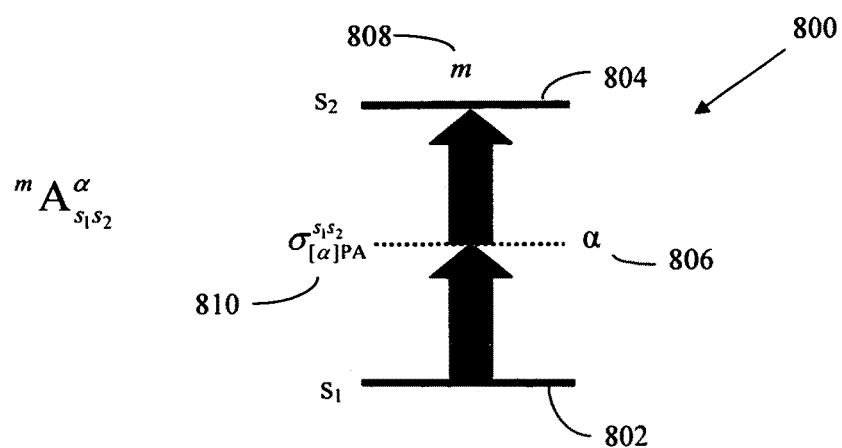
FIG. 8 illustrates an absorption transition module and the associated symbol and parameters.

FIG. 8 illustrates an absorption transition module, which can be symbolized as $^m A_{s_1 s_2}^{\alpha}$. The absorption transition module represents single-/multi-photon absorption ($\alpha > 0$) or stimulated emission ($\alpha < 0$). Below are the absorption transition module parameters:

$s_1/s_2$ indices of the energy levels 802 and 804 the electrons are promoted "from" and "to" (or relaxed "to" and "from", if $\alpha < 0$);

$|\alpha|$ the number 806 of simultaneously absorbed (or inverse absorbed, if $\alpha < 0$) photons;

m index 808 of the spin manifold to which the source and the destination levels belong to.

$\sigma_{[\alpha]PA}^{ss_2}$ absorption molar cross-section parameter 810.

Figure 9A:
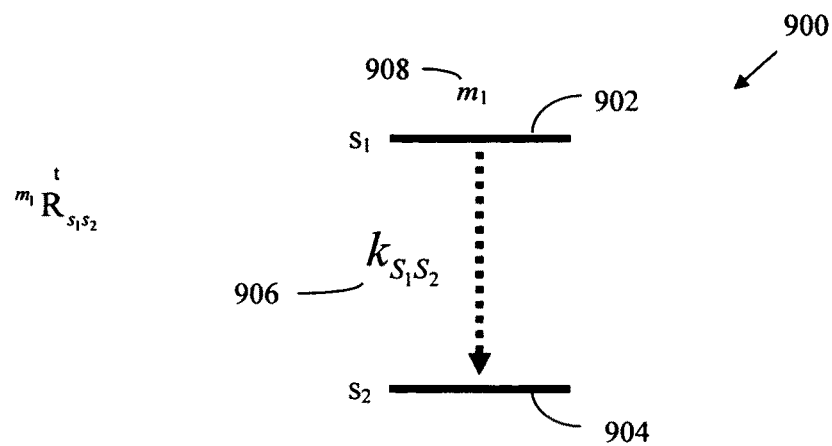
FIG. 9A illustrates a relaxation transition module and the associated symbol and parameters.
Figure 9B:
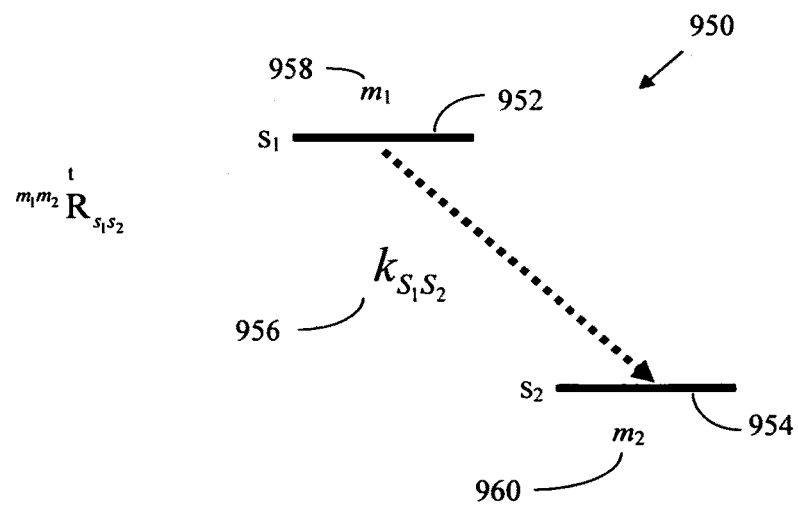
FIG. 9B illustrates another relaxation transition module and the associated symbol and parameters.

FIGS. 9A and 9B illustrate two types of relaxation transition modules, which can be symbolized as $^{m_1 m_2} {}^t R_{s_1 s_2}$. The relaxation transition modules represent electron or exciton transitions from a higher energy state to a lower energy state. The transitions can be between states having the same or different spin manifolds. Below are the relaxation transition module parameters:

$s_1, s_2$ indices of the energy levels the electrons relax "from" and "to";

t (type) type='~' is radiative transfer, and type='–' is non-radiative transfer;

$m_1, m_2$ indices of the spin manifolds for the source and the destination electronic levels;

$k_{s_1 s_2}$ relaxation decay rate parameter.

FIG. 9A represents a relaxation transition module 900 for between two states 902 and 904 of the same spin manifold 908 ($m_1$). The relaxation rate parameter 906 is $k_{s_1 s_2}$. FIG. 9B represents a relaxation transition module 950 for relaxation between two states 952 and 954 having different spin manifolds 958 ($m_1$) and 960 ($m_2$). The relaxation rate parameter is $k_{s_1 s_2}$.

Figure 10A:
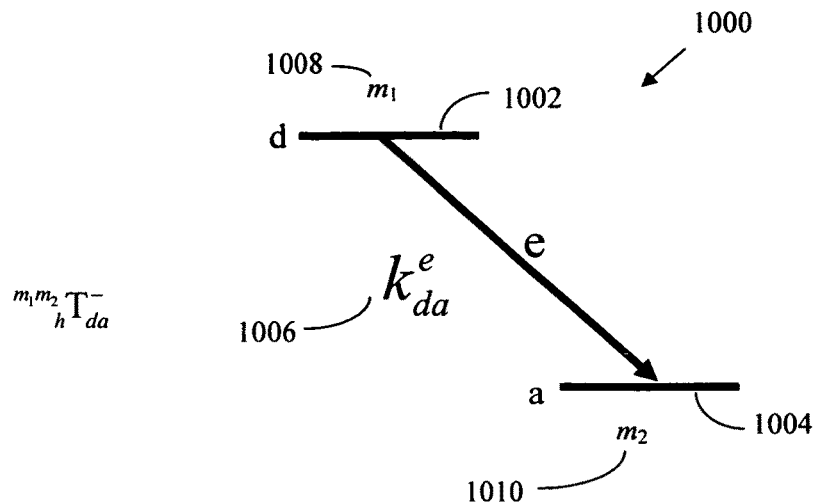
FIG. 10A illustrates an electron transfer transition module and the associated symbol and parameters.
Figure 10B:
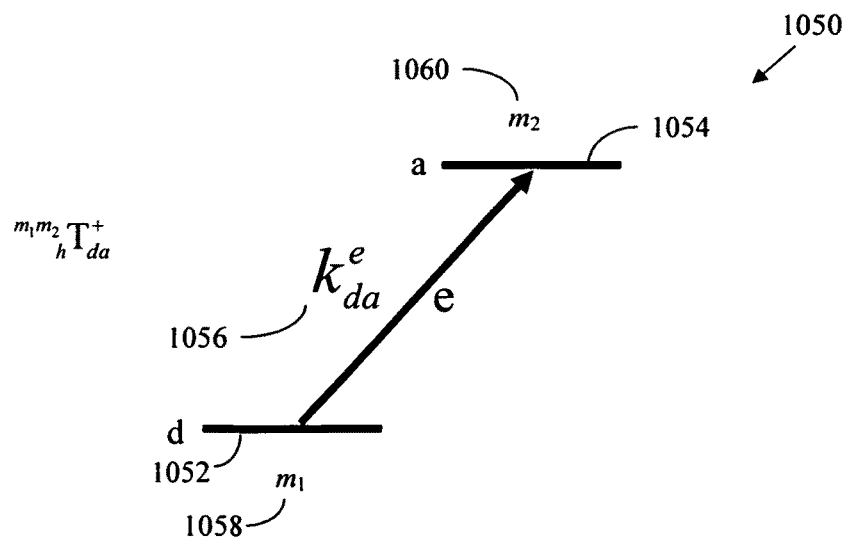
FIG. 10B illustrates another electron transfer transition module and the associated symbol and parameters.

FIGS. 10A and 10B illustrates electron transfer transition modules 1000 and 1050, which can be symbolized as $^{m_1 m_2}_{h}T_{da}^{t}$. The electron transfer is between donor "d" and acceptor "a". The electron transfer (ET) may happen in two different scenarios: (1), an electron "jumps" between a donor, "d", and an acceptor, "a", within one molecule, or (2) an electron "hops" from a donor molecule "d" of a first type to an acceptor molecule "a" of a second type. In the first case, donor and acceptor are bound together in a 1-to-1 complex. In the second case, the donor and acceptor are not bound together and the molecular concentration of "d" may vary with respect to the molecular concentration of "a".

The first type of ET is called intramolecular electron transfer (IET). Transferring electrons can change the total electronic spins of the corresponding donor and acceptor parts. During ET, the total energy, electronic plus vibrational, of the molecule is conserved. However, due to the multiple vibrational levels of both the "d" and "a" portions of the d-a molecule, the electronic energy of the electron may either decrease or increase due to vibrational excitations or de-excitations that occur before or after the actual electron transfer. The rate equations for IET transitions can be described by linear terms in the same way as the relaxation transitions.

The second type of ET is called intermolecular electron transfer. Molecules of two (or more) different types are distributed randomly within a material. The donor "d" is on one type of molecule. The acceptor "a" is on another type of molecule. The concentrations of the molecules of different types should be taken into account in this example since the donor and acceptor are not bound together and the molecular concentration of "d" may vary with respect to the molecular concentration of "a". The rate of ET will be proportional to the product of the concentrations. The resulting mathematical model of population density dynamics will include cross-terms and a new numerical method should be developed.

Referring to FIGS. 10A and 10B, the intramolecular electron transition module parameters for ET transition module $^{m_1 m_2}T_{da}^{type}$ are:

$d(\alpha)$—index of the donor (acceptor) level the electron switches from (to);

type—specification of the direction of the energy transformation of the molecule;
  possible values are
    type='–', de-exciting (default),
    type='+', exciting;

$m_1(m_2)$—index of the spin manifold to which the source (destination) electronic level belongs to.

FIG. 10A represents an intramolecular electron transfer transition module 1000 for electron transfer between donor 1002 and acceptor 1004 having different spin manifolds 1008 ($m_1$) and 1010 ($m_2$). The type is "de-exciting" since the acceptor electronic state has lower energy than the donor. The electron transfer rate parameter 1006 is $k_{da}^{e}$. FIG. 10B represents an intramolecular electron transfer transition module 1050 for electron transfer between donor 1052 and acceptor 1054 having different spin manifolds 1058 ($m_1$) and 1060 ($m_2$). The type is "exciting" since the acceptor electronic state has higher energy than the donor. The electron transfer rate parameter 1056 is $k_{da}^{e}$.

Transition modules for absorption, relaxation and electron transfer are illustrated above. Transition modules can also be utilized to describe energy transfer.

Figure 11:
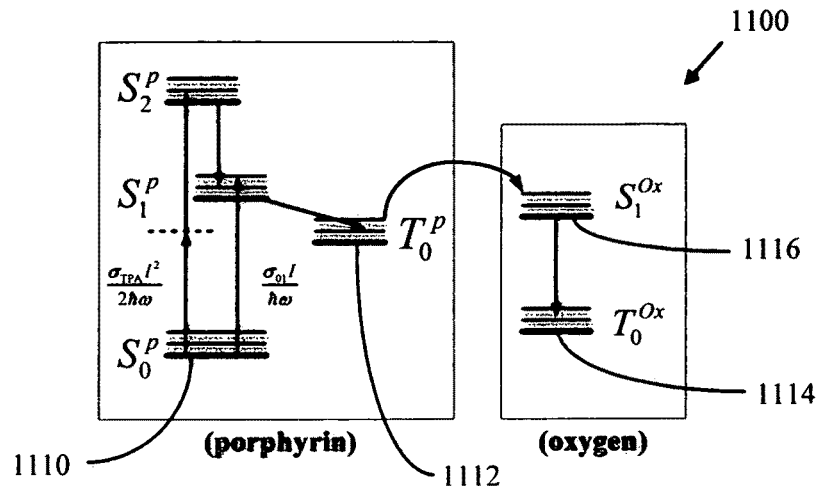
FIG. 11 illustrates the energy level diagrams for energy transfer between a porphyrin molecule and an oxygen molecule.

One type of energy transfer occurs between two molecules and involves relaxation of one of the molecules to a less excited state and the simultaneous excitation of the other molecule due to the just transferred energy. The energy level diagram 1100 in FIG. 11 illustrates an example of energy transfer which occurs between the lowest excited triplet state 1112 ($T_0^P$) of a molecule of porphyrin $T_0^P$ and the triplet ground state 1114 ($T_0^{Ox}$) of molecular oxygen $T_0^{Ox}$.

As a result of the energy transfer between the molecules, the oxygen molecule switches to an excited singlet state 1116 ($S_1^{Ox}$) of oxygen $S_1^{Ox}$, while the porphyrin molecule de-excites to its singlet ground state 1110 ($S_0^P$). The energy gaps of ($T_0^P \rightarrow S_0^P$) and ($T_0^{Ox} \rightarrow S_1^{Ox}$) should be the equal. Due to symmetry, the energy transfer between the porphyrin and oxygen can go in the opposite direction (not shown): from excited oxygen to a ground state porphyrin. The latter process describes a back energy transfer (it can be depicted on the energy level diagram by reversing the curved arrow).

Figure 12:
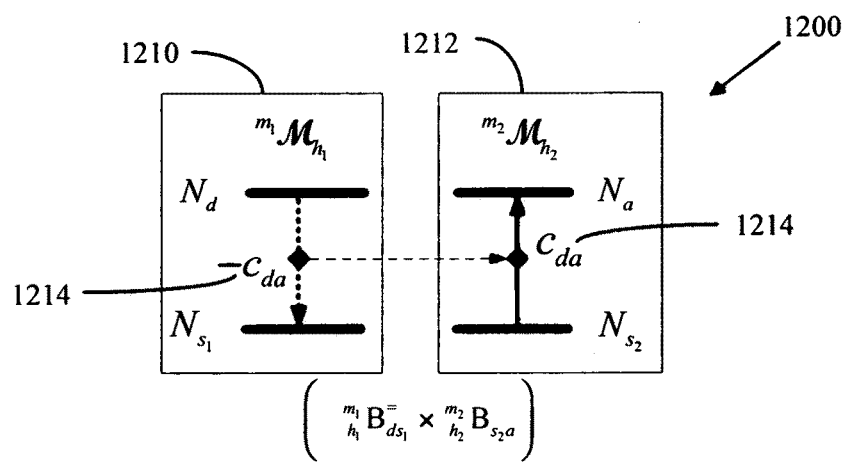
FIG. 12 illustrates an energy transfer transition module and the associated symbol and parameters.

Energy transfer transition module 1200 is illustrated in FIG. 12. In contrast to all the transition modules introduced so far, an energy transfer transition module should consist of two parts: one part 1210 describes a relaxation event in a donor molecule, and the other part 1212 describes an excitation of an acceptor molecule due to the energy transfer between the molecules. Since there are two types of molecules, an extra index is defined which differentiates the spin manifolds of different molecules. An energy transfer module will have a parameter 1214 ($c_{da}$), which is the relaxation (excitation) rate parameter of the donor (acceptor) molecule. In the graphical representation, both transitions—relaxation and excitation—are shown to avoid possible confusion, and the transitions are linked with the broken line.

Here is a detailed explanation of parameters associated with the diagram expression for the energy transfer transition module $_{h_1}^{m_1}B_{ds_1} = \times_{h_2}^{m_2}B_{s_2 a}$ illustrated in FIG. 12:

$h_1(h_2)$—index labels for the donor (the acceptor) molecules;

$s_2, a$ ($d, s_1$)—indices of the energy levels of the molecule $h_2(h_1)$ involved in electron excitation (relaxation) during intermolecular energy transfer;

$m_1(m_2)$—indices of the spin manifolds for the donor (acceptor) molecules involved in the energy transfer energy.

There is also an alternative notation: for brevity, it was not mentioned that the relaxation and/or excitation may happen between energy levels of two different spin manifolds. If this is the case, then all corresponding spin manifold indices should be specified in the left superscript (see Example 1 below):

$$_{h_1}^{m_1 m^1}B_{ds_1} = \times_{h_2}^{m_2 m^2}B_{s_2 a}. \quad (74)$$

Below are fragments of the rate equations which describe forward and backward energy transfer between two molecules labeled as $h_1$ and $h_2$.

For Forward Energy Transfer:

$$_{h_1}^{m_1}B_{ds_1} = \times_{h_2}^{m_2}B_{s_2 a} \quad (75)$$

$$\begin{cases} \ldots \\ \frac{\partial N_d}{\partial \tau} = \ldots -c_{da}N_{s_2}N_d \ldots \\ \frac{\partial N_{s_1}}{\partial \tau} = \ldots +c_{da}N_{s_2}N_d \ldots \\ \ldots \\ \frac{\partial N_a}{\partial \tau} = \ldots +c_{da}N_dN_{s_2} \ldots \\ \frac{\partial N_{s_2}}{\partial \tau} = \ldots -c_{da}N_dN_{s_2} \ldots \\ \ldots \end{cases} \quad (76)$$

For back energy transfer: $_{h_2}{}^{m_2}B_{as_2} {=} \times _{h_1}{}^{m_1}B_{s_1d}$ $$\begin{cases} \ldots \\ \frac{\partial N_a}{\partial \tau} = \ldots -c_{ad}N_{s_1}N_a \ldots \\ \frac{\partial N_{s_2}}{\partial \tau} = \ldots +c_{ad}N_{s_1}N_a \ldots \\ \ldots \\ \frac{\partial N_d}{\partial \tau} = \ldots +c_{ad}N_aN_{s_1} \ldots \\ \frac{\partial N_{s_1}}{\partial \tau} = \ldots -c_{ad}N_aN_{s_1} \ldots \\ \ldots \end{cases} \quad (77)$$

Energy transfer may also happen between molecules of the same type (for example, energy-transfer upconversion between Er atoms in Er-doped silica optical fibers). This process sometimes is called energy migration. Such events can be described in the transition module framework by an energy transfer transition module $_h{}^{m_1m^1}B_{ds}{=}\times_h{}^{m_1m^1}B_{da}$, or one could rewrite it as the following squared expression $(_h{}^{m_1m^1}B_{da})^2$. However, such a transition module would not change the rate equations since according to the system of equations (76) all cross terms should cancel each other. As far as an even distribution of molecules is assumed, under this model the migration event cannot be included to the mathematical model.

Example 1

Porphyrin-Oxygen Energy Transfer Transition Modules

Figure 13:
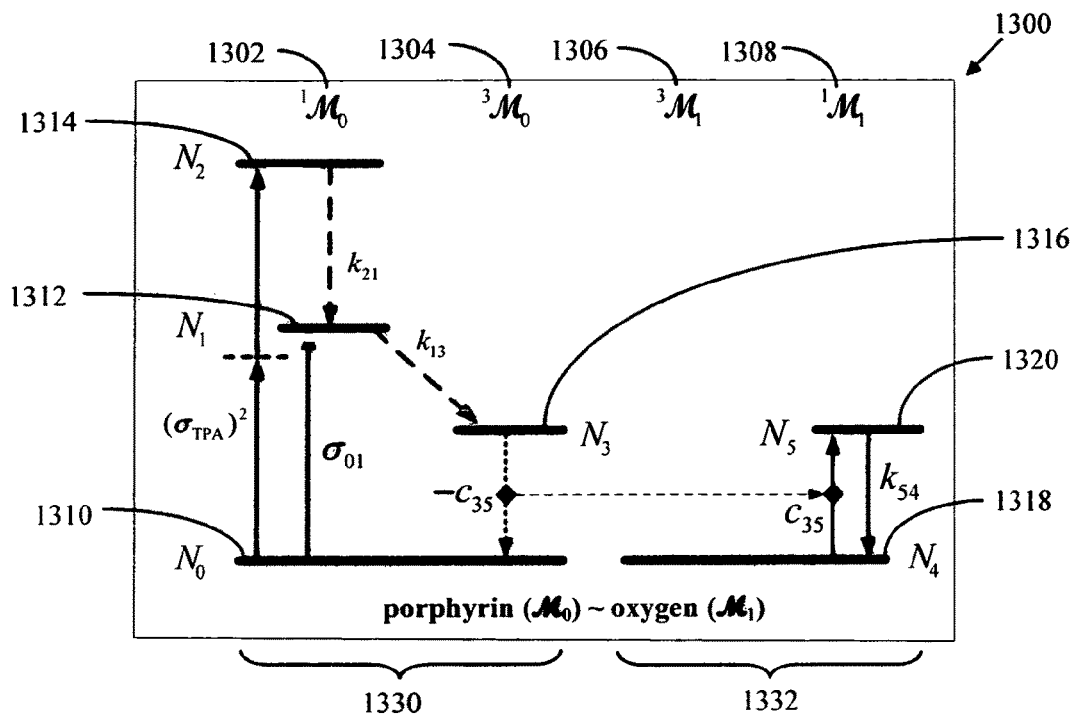
FIG. 13 shows an energy level diagram for a porphyrin molecule and an oxygen molecule and illustrates an example of an energy transfer transition module.

FIG. 13 is a graphical representation of the energy level diagrams 1300 of porphyrin 1330 and oxygen 1332 within the framework of the transition module framework. In the energy level diagrams 1300, the spin manifolds $\mathcal{M}$ of the molecules are labeled as follows: h=0 is for porphyrin 1330 and h=1 is for oxygen 1332. The energy levels of porphyrin are divided into two groups: 1302 ($^1\mathcal{M}_0$) for its singlet states and 1304 ($^3\mathcal{M}_0$) for its triplet states. The same is done for the oxygen: 1308 ($^1\mathcal{M}_1$) for its singlet states and 1306 ($^3\mathcal{M}_1$) for its triplet states. The graphical diagram has six levels in total (1310, 1312, 1314, 1316, 1318 and 1320): four levels (1310, 1312, 1314 and 1316) belong to the porphyrin molecule and two levels (1318 and 1320) belong to the oxygen molecule.

Figure 14:
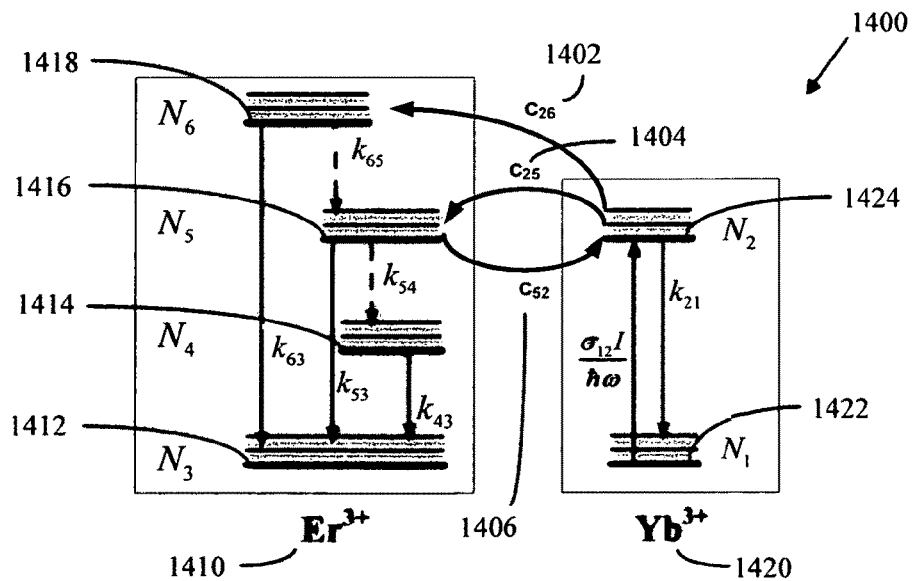
FIG. 14 shows energy level diagrams for energy transfer upconversion between an erbium ion and an ytterbium ion.

In another type of energy transfer (illustrated schematically in FIG. 14) known as energy transfer upconversion, two ions that are initially both in excited states exchange energy. After the energy transfer, one ion drops to a lower energy state and the other ion jumps to a higher excited state. During energy transfer upconversion, the electrons are promoted to higher energy levels from excited states, not necessarily from the ground state. The upconversion process, which occur in $Er^{3+}$-$Yb^{3+}$ πcodoped Ti:LiNbO3 optical amplifiers, is a good example of the energy transfer upconversion between ions of two different types. In its shorter form, the energy level diagram 1400 of ions $Er^{3+}$ and $Yb^{3+}$ is shown in FIG. 14.

The curved arrow labeled by 1402 ($c_{26}$) on the figure represents energy transfer upconversion which promotes a first ion 1410 ($Er^{3+}$) from an excited state 1416 ($N_5$) to a higher excited energy state 1418 ($N_6$), while a second ion 1420 ($Yb^{3+}$) relaxes from the excited state 1424 ($N_2$) to the ground state 1422 ($N_1$). The energy gap between the states $N_5$ and $N_6$, and between the states $N_1$ and $N_2$ should be equal. The other curved arrows labeled by 1404 ($c_{25}$) and 1406 ($c_{52}$) represent the energy transfer and the back energy transfer transitions which were described in the previous section and which do not include upconversion of an electron from an excited state to a higher excited state.

Figure 15:
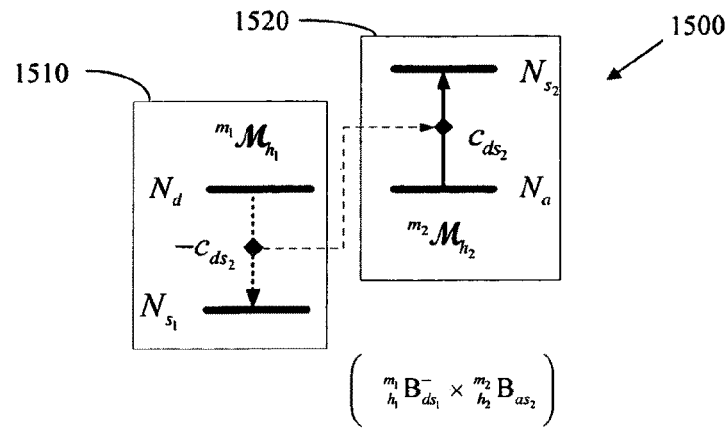
FIG. 15 illustrates an energy transfer upconversion transition module and the associated symbol and parameters.

FIG. 15 illustrates a graphical representation of a new energy transfer upconversion transition module 1500 which encodes the energy transfer upconversion event. One portion 1510 of the upconversion transition module 1500 represents the transition of an electron from an excited state to a lower energy level. The other portion 1520 represents the upconversion of an electron from an excited state to a higher excited state. Listed below are the parameters associated with the energy transfer upconversion transition module $_{h_1}{}^{m_1}B_{ds_1}{}^{-}\times _{h_2}{}^{m_2}B_{as_2}$:

$h_1(h_2)$—index labels for the donor (the acceptor) molecule;

$a,s_2(d,s_1)$—indices of the energy levels for the acceptor (donor) molecule $h_2(h_1)$ involved in electron excitation (relaxation) during intermolecular energy transfer;

$m_1(m_2)$—indices of the spin manifolds for the donor (acceptor) molecules.

The following is an alternative notation for the energy transfer upconversion transition module: for brevity, it was not mentioned that the relaxation (excitation) may happen between energy levels of two different spin manifolds. If this is the case, then all corresponding spin manifold indices should be specified in the left superscript (see Example 2 below): $_{h_1}{}^{m_1m^1}B_{ds_1}{}^{-}\times _{h_2}{}^{m_2m^2}B_{as_2}$.

Below are fragments of the rate equations which describe energy transfer upconversion between two molecules labeled as $h_1$ and $h_2$. In this case, the energy transfer upconversion transition module is:

Energy transfer: $_{h_1}{}^{m_1}B_{ds_1}{}^{-}\times _{h_2}{}^{m_2}B_{as_2}$ $$\begin{cases} \ldots \\ \frac{\partial N_d}{\partial \tau} = \ldots -c_{ds_2}N_aN_d \ldots \\ \frac{\partial N_{s_1}}{\partial \tau} = \ldots +c_{ds_2}N_aN_d \ldots \\ \ldots \\ \frac{\partial N_a}{\partial \tau} = \ldots +c_{ds_2}N_dN_a \ldots \\ \frac{\partial N_{s_2}}{\partial \tau} = \ldots -c_{ds_2}N_dN_a \ldots \\ \ldots \end{cases} \quad (78)$$

Example 2

Figure 16:
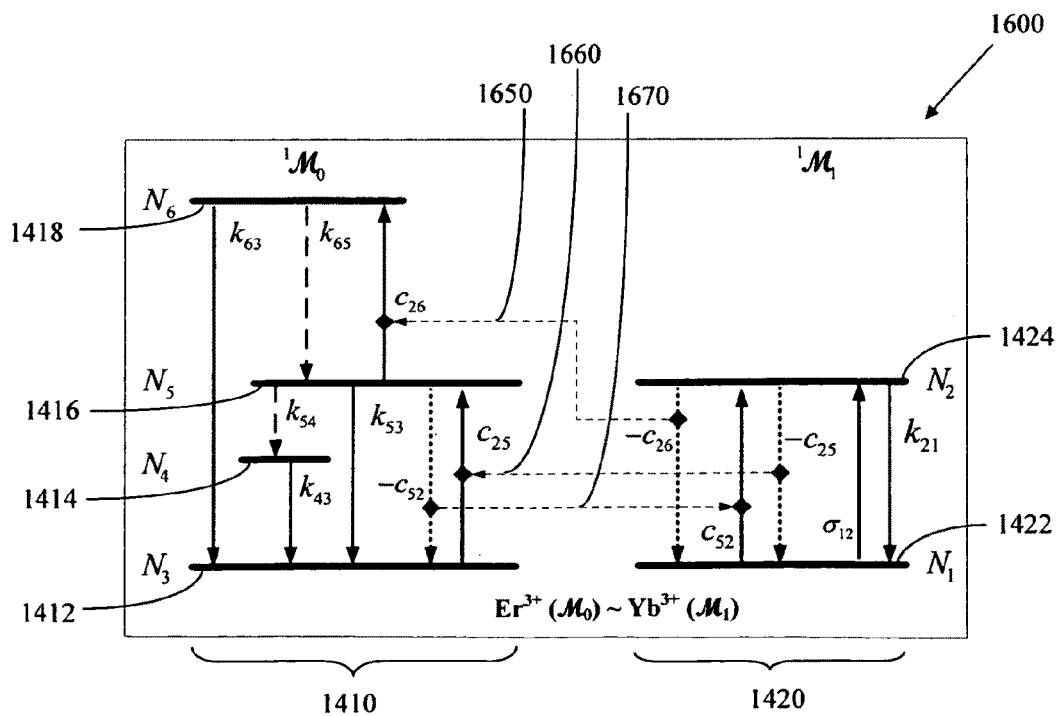
FIG. 16 shows energy level diagrams and the associated transition modules for energy transfer upconversion and energy transfer between an erbium ion and an ytterbium ion.

Illustrates $Er^{3+}-Yb^{3+}$ Energy Transfer and Energy Transfer Upconversion Transition Modules FIG. 16 is another graphical representation 1600 of the energy level diagram for the $Er^{3+}-Yb^{3+}$ interactions that were illustrated in FIG. 14 and that follow the principles of the framework of transition modules. The ion labels and energy level labels in FIG. 14 are repeated in FIG. 16. Both energy transfer and energy transfer upconversion processes are shown in FIG. 16.

An example of energy transfer upconversion transition module 1500 (FIG. 15) is shown by the coupled transitions connected by dotted line 1650. A first electron in excited state 1424 ($N_2$) drops to a lower energy state 1422 ($N_1$) and transfers energy to a second electron in excited state 1416 ($N_5$), promoting the second electron to a higher excited energy state 1418 ($N_6$). Energy is conserved in the transfer.

Two examples of the energy transfer transition module 1200 (FIG. 12) are also illustrated in FIG. 16. One example is shown by the coupled transitions connected by dotted line 1660. A first electron in excited state 1424 ($N_2$) drops to a lower energy state 1422 ($N_1$) and transfers energy to a second electron in state 1412 ($N_3$), promoting the second electron to excited state 1416 ($N_5$). Another example is shown by the coupled transitions connected by dotted line 1670. A first electron in excited state 1416 ($N_5$) drops to a lower energy state 1412 ($N_3$) and transfers energy to a second electron in state 1422 ($N_1$), promoting the second electron to excited state 1424 ($N_2$). Both transitions conserve energy.

Figure 17:
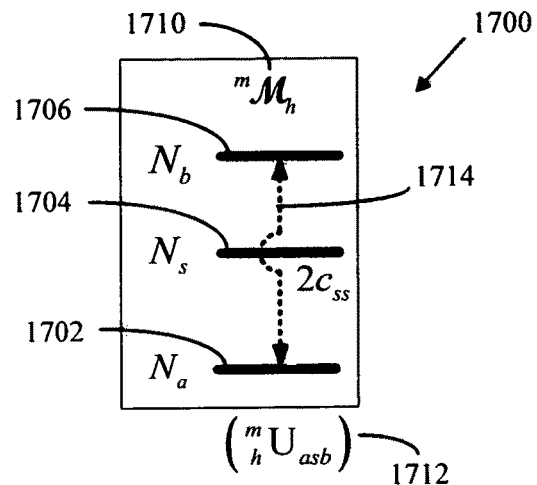
FIG. 17 illustrates another type of energy transfer upconversion transition module and the associated parameters.

Another type of energy transfer upconversion transition module involves energy exchange between two excited molecules (or ions) of the same type being in close proximity. During such interaction, one of the excited molecules (donor) releases energy by de-exciting to a ground state, while the other excited molecule (acceptor) is promoted to a higher excited energy level due to the released energy. This interaction is denoted by a single upconversion transition module 1700 depicted in FIG. 17. The two-way arrow 1714 in tb he picture represents excitation of a donor molecule from level 1704 ($N_s$) to level 1706 ($N_b$), and de-excitation of an acceptor molecule from level 1704 ($N_s$) to level 1702 ($N_a$). Both molecules are of the same type and belong to spin manifold 1710 ($^m\mathcal{M}_a$).

The following is a list of the associated parameters in the diagram expression 1700 for the upconversion transition module 1700 ($_h^m U_{asb}$):

h—index of the molecule where upconversion event occurs;
a(b)—index of the energy level an electron relaxes to (excites to) from the energy level s during upconversion process;
m—index of the spin manifold of the molecule h which is involved in upconversion.

There is also an alternative notation when only one type of molecule is presented. In this case, one can omit the molecular index h: $^m U_{asb} \equiv {_0^m}U_{asb}$.

Below are fragments of the rate equations which describe upconversion process within a molecule or ion labeled as h and the upconversion transition module is $_h^m U_{asb}$.

$$\begin{cases} \cdots \\ \frac{\partial N_a}{\partial \tau} = \cdots + c_{ss}N_s^2 \cdots \\ \frac{\partial N_s}{\partial \tau} = \cdots - 2c_{ss}N_s^2 \cdots \\ \frac{\partial N_b}{\partial \tau} = \cdots + c_{ss}N_s^2 \cdots \\ \cdots \end{cases} \quad (79)$$

Example 3

$Er^{3+}$ Doped Phosphate Glass

Figure 18:
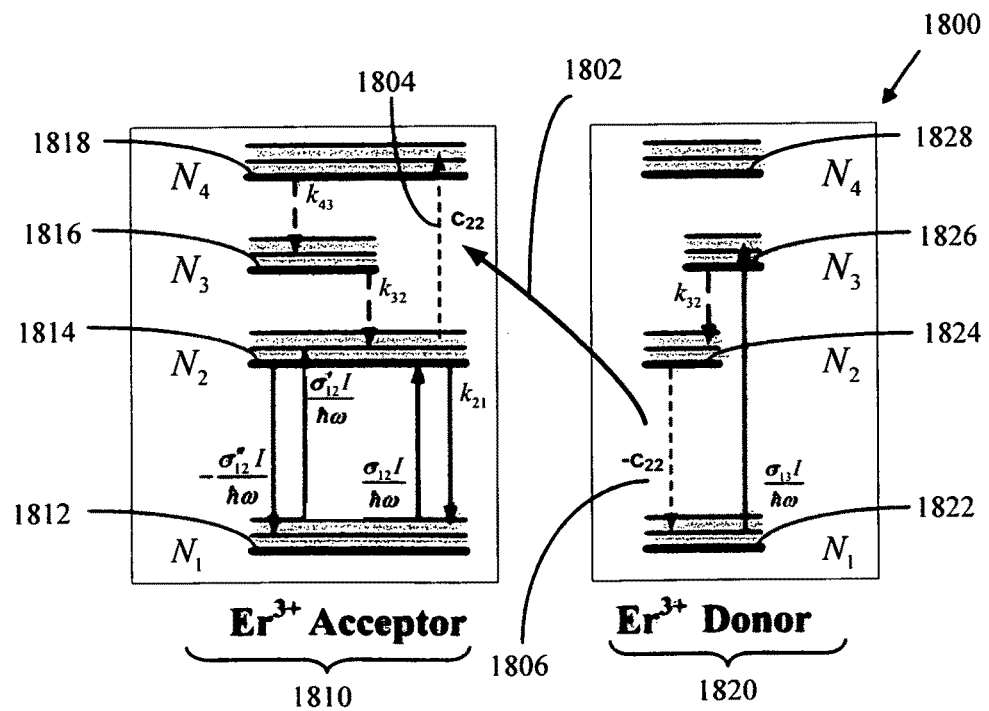
FIG. 18 shows energy level diagrams for energy transfer upconversion between a first erbium ion and a second erbium ion.

An $Er^{3+}$ doped glass amplifier is based on the phenomenon of cooperative-upconversion when two close $Er^{3+}$ ions interact by transferring energy. The energy level diagram 1800 in FIG. 18 illustrates interacting $Er^{3+}$ ions 1810 and 1820. The curved arrow 1802 and the dotted arrows 1804 and 1806 represent the upconversion event.

Figure 19:
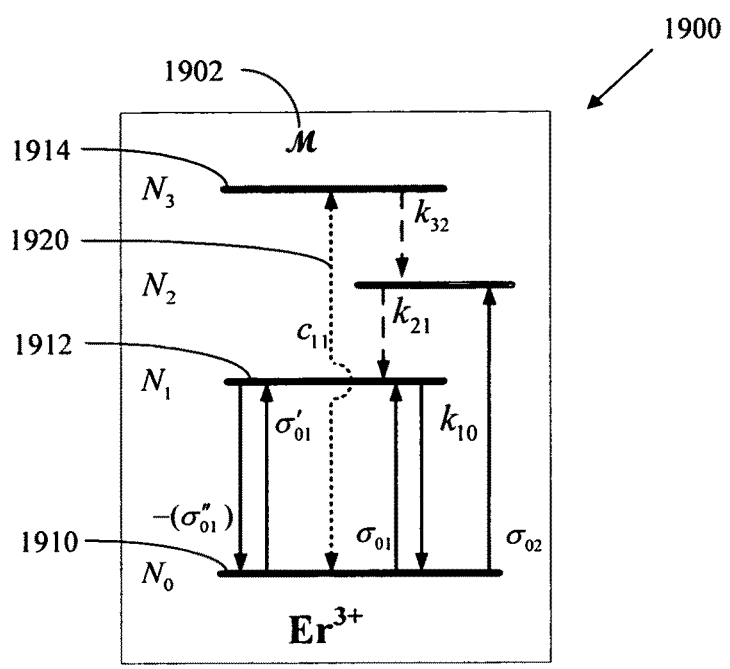
FIG. 19 illustrates another way to show the energy level diagram for energy transfer upconversion between a first erbium ion and a second erbium ion and also illustrates an energy transfer upconversion transition module.

Within the transition module framework, the interaction of the two ions will have the graphical representation 1900 as shown in FIG. 19. The two-way arrow 1920 in the picture represents excitation of a donor ion from level 1912 ($N_1$) to level 1914 ($N_3$), and de-excitation of an acceptor ion from level 1912 ($N_1$) to level 1910 ($N_0$). Note that the transition module diagram 1900 has only one spin manifold 1902 ($\mathcal{M}$); therefore, the spin manifold index is left unspecified in the module expression. The same applies for the index of the ion h=0, as there is only one type of ion that interacts.

The transition modules are all summarized in the following table (in the table, the word "molecule" includes any type of optically responsive material including, for example, chromophores, molecules or ions):

| Set | Module title | Diagram expression | Molecules involved | Comments |
|---|---|---|---|---|
| $\mathcal{A}$ | Absorption transition module | $_h^m A_{s_1 s_2}{}^a$ (if one molecule $^m A_{s_1 s_2}{}^a$) | Within same molecule. | A molecular index h was added to the diagram expression. |
| $\mathcal{R}$ | Relaxation transition module | $_h^{m_1 m_2} R_{s_1 s_2}^t$ (if only one type of molecule, then $^{m_1 m_2} R_{s_1 s_2}^t$) | Within same molecule. | A molecular index h was added to the diagram expression. |
| $\mathcal{T}$ | Electron transfer transition module | $^{m_1 m_2}_h T_{s_1 s_2}^t$ (if only one type of molecule, then $^{m_1 m_2} T_{s_1 s_2}^t$) | Between molecular parts or between two molecules. | Describes an electron transfer within one molecule labeled by h, which transforms the molecule from state $s_1$ to state $s_2$. |

-continued

| Set | Module title | Diagram expression | Molecules involved | Comments |
|---|---|---|---|---|
| $\mathcal{B}_e$ | Energy transfer transition module | Energy transfer $_{h_1}{}^{m1}B_{ds_1}{}^- \times {}_{h_2}{}^{m2}B_{s_2 a}$ Energy transfer upconversion $_{h_1}{}^{m1}B_{ds_1}{}^- \times {}_{h_2}{}^{m2}B_{as_2}$ | Between two molecules of different types. | Describes an energy transfer and an energy transfer upconversion, respectively, from a donor molecule $h_1$ to an acceptor molecule $h_2$, which transforms the involved molecules to different (excited/de-excited) states. Energy transfer involves ground states, while energy transfer upconversion involves mostly excited states. |
| $\mathcal{U}_e$ | Upconversion transition module | $_h{}^m U_{asb}$ (if only one type of molecule, then $^m U_{asb}$) | Between two molecules of same type. | Describes an upconversion from the state s within the molecule labeled h. |

For the electron transfer transition modules and the various energy transfer transition modules, the mathematical equations need to be modified.

Solutions to the beam propagation equations need to be extended to define a unique map from the new set of transition modules to the corresponding terms in the extended beam propagation equations, and to develop a potentially robust numerical scheme to solve the new set of beam propagation equations. First, one must add necessary new terms to the rate equations. Second, one must iteratively build the matrices $D_\alpha$ of the rate equations from the diagram expressions of new transition modules. Finally, one must determine a numerical solution of the resulting new set of beam propagation equations.

Electron transfer transition modules do not require any modification from the original model of building modules. The rate parameters of electron transfer, $k_{da}{}^e$, are added to the corresponding elements of matrix $D_0$, so that the shape of the beam propagation equations and, therefore, the original numerical algorithm to solve the equations do not change. For a given diagram expression $e = {}^{m_1 m_2}T_{da}{}^{type}$ of an ET transition module with its transition rate parameter, $k_{da}{}^e$, one can update the matrix $D_0$ by adding or subtracting the rate parameter as follows $$D_0[d,d] = D_0[d,d] - k_{da}{}^e, \quad (80)$$

$$D_0[a,d] = D_0[a,d] + k_{da}{}^e. \quad (81)$$

Adding transition modules for energy transfer and upconversion requires including extra terms to the original beam propagation equations. Energy transfer may occur between two molecules of different types; therefore, one needs to include the population densities of all energy levels of the molecules to the overall vector of population densities $N(\eta, \rho, \tau)$:

$$N = [\underbrace{N_0, \ldots, N_{S_0-1}}_{h=0}, \underbrace{N_{S_0}, \ldots, N_{S_0+S_1-1}}_{h=1}, \ldots, \quad (82)$$

$$\underbrace{N_{S_0+S_1+\ldots+S_{N_H-2}}, \ldots, N_{S_0+S_1+\ldots+S_{N_H-1}-1}}_{h=N_H-1}]^T,$$

so that a molecule with index h has $S_h$ components within the total vector $N(\eta,\rho,\tau)$ starting from index $$\sum_{i=0}^{h-1} S_i \text{ to index } \left(\sum_{i=0}^{h} S_i\right) - 1 : N_{S_0+S_1+\ldots+S_{h-1}}, \ldots, N_{S_1+S_2+\ldots+S_h-1},$$

In this case, a nonlinear material is a composite consisting of $N_H$ different molecules. Having chosen the global indexing of the energy levels of all the molecular components [see Eq. (82)], the algorithm for construction of matrices $D_\alpha$ from the original set of transition modules for absorption and relaxation (and adding the electron transfer transition modules) does not change. However, for the energy transfer and upconversion transition modules, the cross terms defined by Eqs. (76), (77), (78), and (79) should be included in the rate equations. One adds a certain matrix $D_{egy}$ to the rate equation operator $Y_{rate}$ defined previously in the text by Eq. (46), resulting in the following equation:

$$Y'_{rate}(\eta, \rho, \tau) = d_0 D_0 + d_0 D_{egy} + \sum_{\alpha=1}^{N_A} d_\alpha D_\alpha \overline{Q}^\alpha(\eta, \rho, \tau) \quad (83)$$

$$\equiv Y_0 + Y^N(\eta, \rho, \tau) + \sum_{\alpha=1}^{N_A} Y_\alpha^Q(\eta, \rho, \tau),$$

So that now the beam propagation equations become $$\frac{\partial N(\eta, \rho, \tau)}{\partial \tau} = \left[d_0 D_0 + d_0 D_{egy} + \sum_{\alpha=1}^{N_A} d_\alpha D_\alpha \overline{Q}^\alpha(\eta, \rho, \tau)\right] N(\eta, \rho, \tau) \quad (84)$$

$$\frac{\partial Q(\eta, \rho, \tau)}{\partial \eta} = \left[-\sum_{\beta=1}^{N_B} g_\beta (\sigma_\beta \cdot N(\eta, \rho, \tau)) \overline{Q}^{\beta-1}(\eta, \rho, \tau) + \right. \quad (85)$$

$$\left. \frac{i}{4} \nabla_\rho^2 + i \sum_{\gamma=1}^{N_\chi} p_{2\gamma+1} \overline{Q}^\gamma(\eta, \rho, \tau) - c_L\right] Q(n, \rho, \tau)$$

To uniquely map the transition modules from energy transfer and upconversion to corresponding terms in the rate equations (84), one considers the following three cases for a photoactivated material with a diagram expression e (for energy transfer) in it:

Case 1.) e is an expression for an energy transfer transition module, $_{h_1}{}^{m_1}B_{ds_1}{}^=\times_{h_2}{}^{m_2}B_{s_2a}$, with the transfer rate $c_{da}$; one adds the following terms to the matrix $D_{egy}$ according to Eq. (76):

$$D_{egy}[d,d]=D_{egy}[d,d]-c_{da}N_{s_2}, \quad (86)$$

$$D_{egy}[s_1,d]=D_{egy}[s_1,d]+c_{da}N_{s_2}, \quad (87)$$

$$D_{egy}[a,s_2]=D_{egy}[a,s_2]+c_{da}N_d, \quad (88)$$

$$D_{egy}[s_2,s_2]=D_{egy}[s_2,s_2]-c_{da}N_d. \quad (89)$$

Case 2.) e is an expression for an energy transfer upconversion transition module, $_{h_1}{}^{m_1}B_{ds_1}{}^-\times_{h_2}{}^{m_2}B_{as_2}$, with the transfer rate $c_{da}$; one adds the following terms to the matrix $D_{egy}$ according to Eq. (78):

$$D_{egy}[d,d]=D_{egy}[d,d]-c_{ds_2}N_a, \quad (90)$$

$$D_{egy}[s_1,d]=D_{egy}[s_1,d]+c_{ds_2}N_a, \quad (91)$$

$$D_{egy}[a,a]=D_{egy}[a,a]-c_{ds_2}N_d, \quad (92)$$

$$D_{egy}[s_2,a]=D_{egy}[s_2,a]+c_{ds_2}N_d. \quad (93)$$

Case 3.) e is an expression for an upconversion transition module, $_h{}^m U_{asb}$, with the transfer rate $c_{ss}$; one adds the following terms to the matrix $D_{egy}$ according to Eq. (79):

$$D_{egy}[a,s]=D_{egy}[a,s]+c_{ss}N_s, \quad (94)$$

$$D_{egy}[s,s]=D_{egy}[s,s]-2c_{ss}N_s, \quad (95)$$

$$D_{egy}[b,s]=D_{egy}[b,s]+c_{ss}N_s. \quad (96)$$

To provide consistency, one observes that the upconversion transition modules are equivalent to the energy transfer upconversion transition modules. Indeed, if one considers energy transfer upconversion within one molecule then one expects that $$_0{}^m U_{asb}[c_{ss}] \sim _0{}^m B_{sa}{}^- \times _0{}^m B_{sb}[c_{ss}]. \quad (97)$$

According to the definition of $_0{}^m B_{sa}{}^- \times _0{}^m B_{sb}[c_{ss}]$ and the building process given by Eqs. (90)-(93), the rate equations for this module will have the following terms:
$\partial N_s/\partial \tau = \ldots -c_{ss}N_s^2 \ldots -c_{ss}N_s^2$, $\partial N_a/\partial \tau = \ldots +c_{ss}N_s^2$, and $\partial N_b/\partial \tau = \ldots +c_{ss}N_s^2$. The terms coincide with terms corresponding to the module $_0{}^m U_{asb}[c_{ss}]$. Q.E.D.

A variant of Crank-Nicholson numerical integration scheme developed for the original beam propagation equation, which may be given by equations [58] and [59], is used to take into account new transitions.

The numerical integration for the propagation equation (85) stays the same.

Figure 20A:
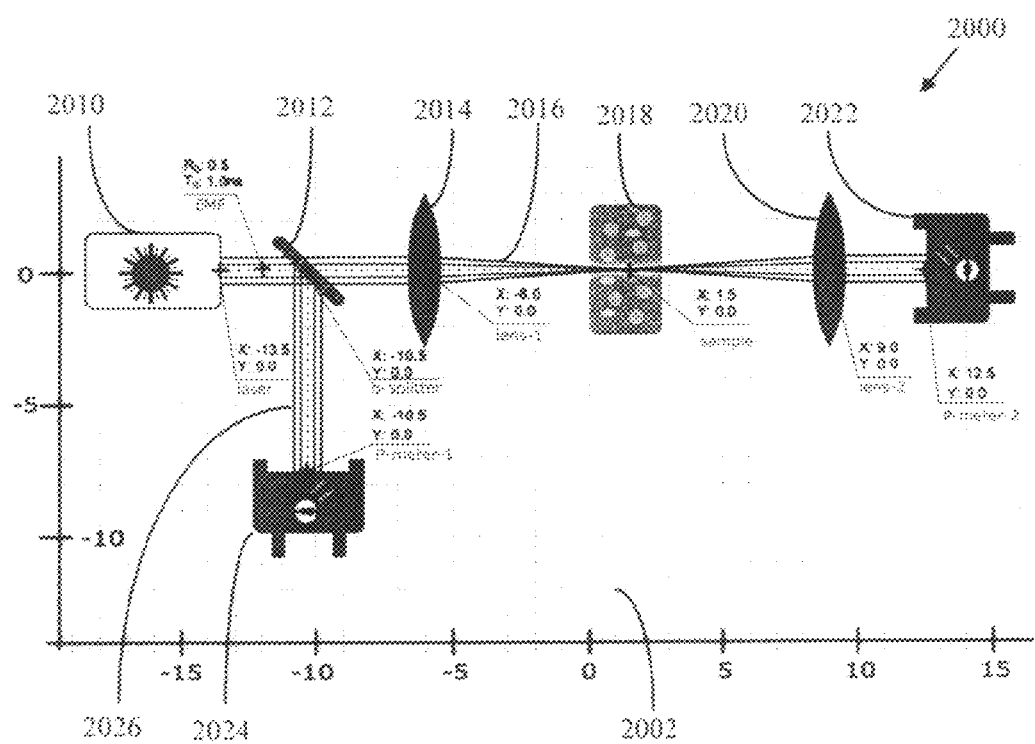
FIG. 20A is an illustration of a designer window for experimental computer aided design. The sample is a single layer of either a homogeneous or a composite material.

Another embodiment of this invention is to add an optional step to the method embodiments illustrated as flow diagram 600 in FIG. 6A and flow diagram 650 in FIG. 6B. The optional step is to provide an experimental CAD (E-CAD) GUI feature that displays a separate toolbox and a separate designer window to design and display a schematic representation of the experimental arrangement used to measure the interaction of electromagnetic radiation with a material. The toolbox can include schematic representation of pieces of experimental apparatus, such as a laser, a lens, a sample and a detector. The designer window can display a schematic representation of the experimental arrangement. An icon representing a sample may be applied several times to build a layered material in the designed window. Photophysical parameters and an energy level diagram can be assigned to each layer separately by using the material CAD designer window. An example representation 2000 of an experimental arrangement in a GUI designer window is illustrated in FIG. 20A. Another example 2050 is illustrated in FIG. 20B.

FIG. 20A shows an E-CAD GUI designer window 2000 for an experimental nonlinear transmission measurement. Graphical symbols of experimental components are taken from an experimental toolbar (not shown) and placed on a grid 2002 representing a virtual optical table. In this example, the experimental components are a laser 2010, a beam splitter 2012 and a detector 2024 for monitoring the laser power, a focusing lens 2014, the sample material 2018, a collecting lens 2020 and the detector 2022 for the primary beam 2016. The contour beam representation 2016 was chosen do visualize the beam propagation through the virtual setup. The sample material 2018 consists of one layer. The single layer can have a homogeneous composition or can be a composite material with more than one composition.

Figure 20B:
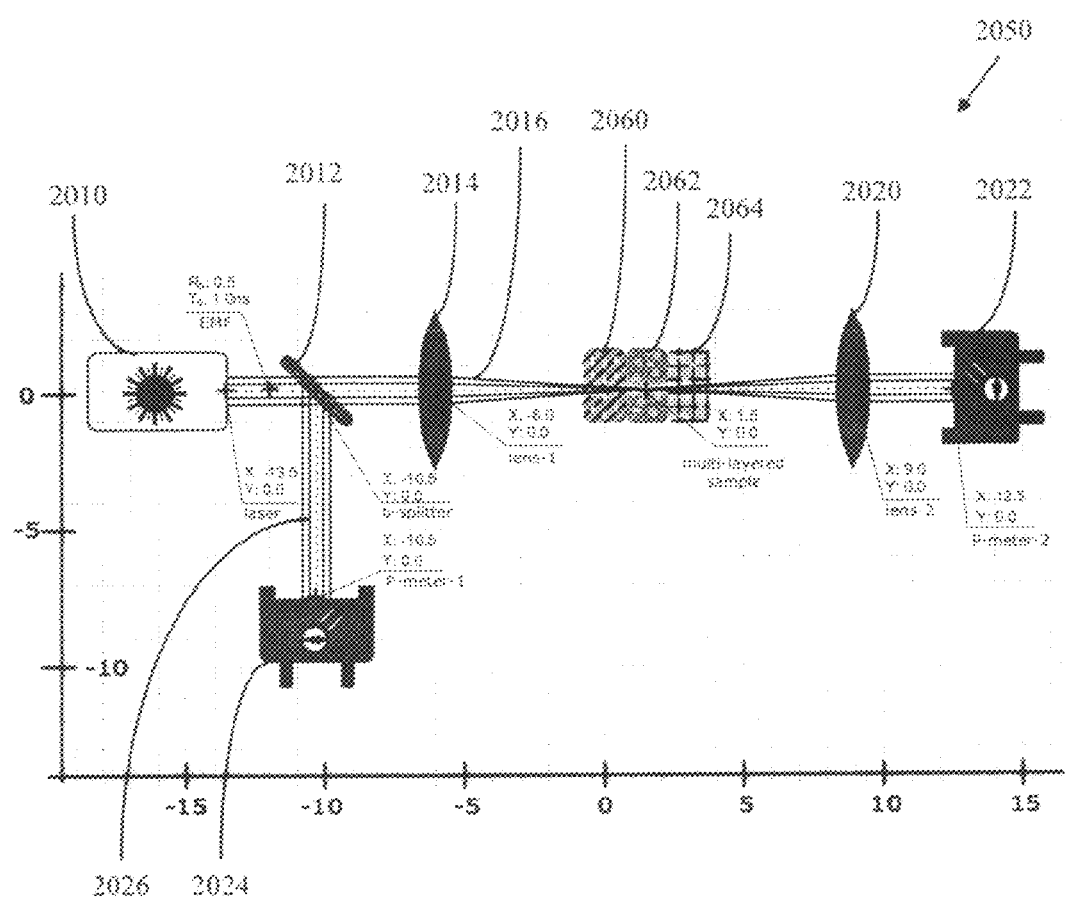
FIG. 20B is another illustration of a designer window for experimental computer aided design. The sample is composed of three layers of different compositions.

FIG. 20B shows another E-CAD GUI designer window 2050 for an experimental nonlinear transmission measurement. The sample materials in FIG. 20B consists of three layers labeled 2060, 2062 and 2064. Each layer can have a different composition, either homogeneous or heterogeneous.

Figure 21A:
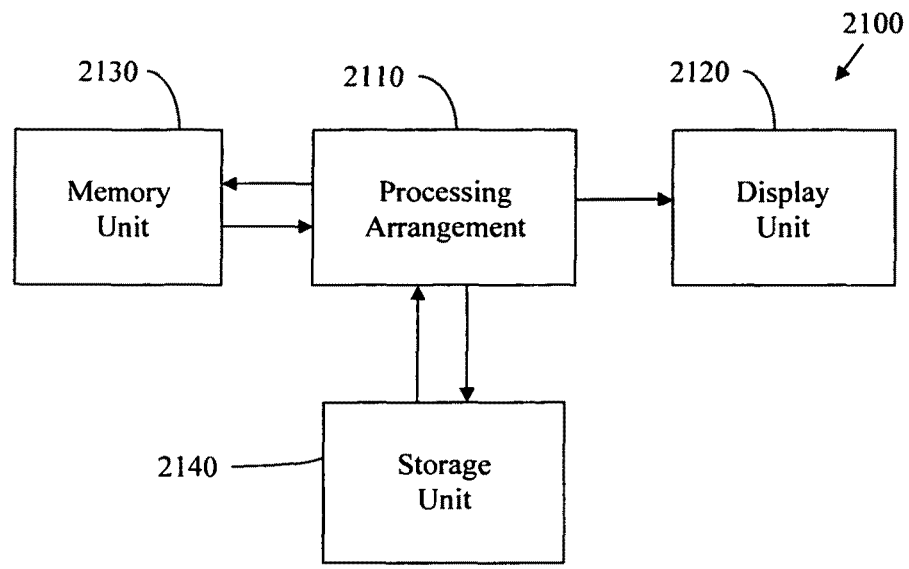
FIG. 21A is an example of a system for analyzing the interaction between electromagnetic radiation and a material.

Another embodiment of this invention is a system 2100 illustrated in FIG. 21A for analyzing an interaction between electromagnetic radiation and a material. The system 2100 includes a processing arrangement 2110 for executing computer programs, a display unit 2120 having at least one display screen, a memory unit 2130 and a storage arrangement 2140 that stores the results generated by the application program.

The memory unit 2130 of the system stores an application program that includes first executable instructions operable on the system for determining the interaction between the electromagnetic radiation and the material and second executable instructions operable on the system for displaying a graphical user interface on the display unit.

The graphical user interface includes the functionality to show a toolbox and a designer window on the display unit 2120. The toolbox includes a set of icons. The set of icons includes a first icon that represents an energy level for the material and at least a second icon that represents an element of a plurality of transition modules for the material. Each icon that represents an element of a plurality of transition modules also corresponds to at least one associated parameter in the application program.

The designer window is configured to present the plurality of energy levels for the material and the plurality of transition modules in the material. If the interaction involves two or more materials or involves a layered material having two or more compositions, the designer window can present the energy levels and transition modules for the two or more materials in one designer window or in multiple designer windows.

The graphical user interface allows the user to move a copy of the first icon from the toolbox to the designer window and thereby modify, within the designer window, the plurality of energy levels. The graphical user interface also allows the user to move a copy of the second icon from the toolbox to the designer window and thereby modify, within the designer window, the plurality of transition modules for the material. At the same time, the parameters associated with the second icon are incorporated into the application program.

Figure 21B:
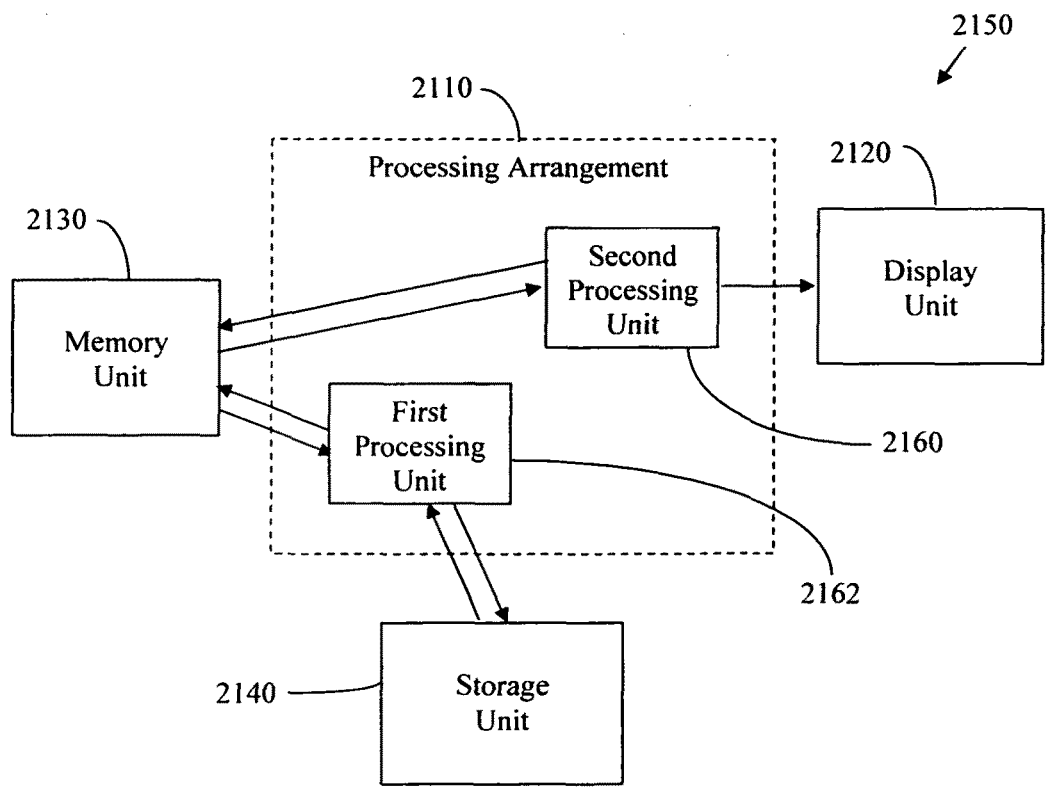
FIG. 21B is another example of a system for analyzing the interaction between electromagnetic radiation and a material.

The processing arrangement 2110 can be a single computer processor as illustrated in FIG. 21A or multiple computer processors or cores as shown in FIG. 21B. FIG. 21B illustrates a system 2150 with two processing units 2160 and 2162 in the processing arrangement 2110. For example, the processing arrangement 2110 can include a first processing unit 2162 for executing the first executable instructions operable on the system for determining the interaction between the electromagnetic radiation and the material and a second processing unit 2160 for executing the second executable instructions operable on the system for displaying the graphical user interface on the display unit. The processing arrangement with multiple processing units can also be split into multiple locations (not shown), so that a computer processor on a remote server can run the mathematical calculations and a local computer processor can handle the display unit with its graphical user interface.

Another embodiment of this invention is a computer-based method for analyzing an interaction between electromagnetic radiation and a material. The material includes a single layer or composition or the material includes two or more different layers or the material includes at least one layer that includes at least two different compositions.

Figure 22A:
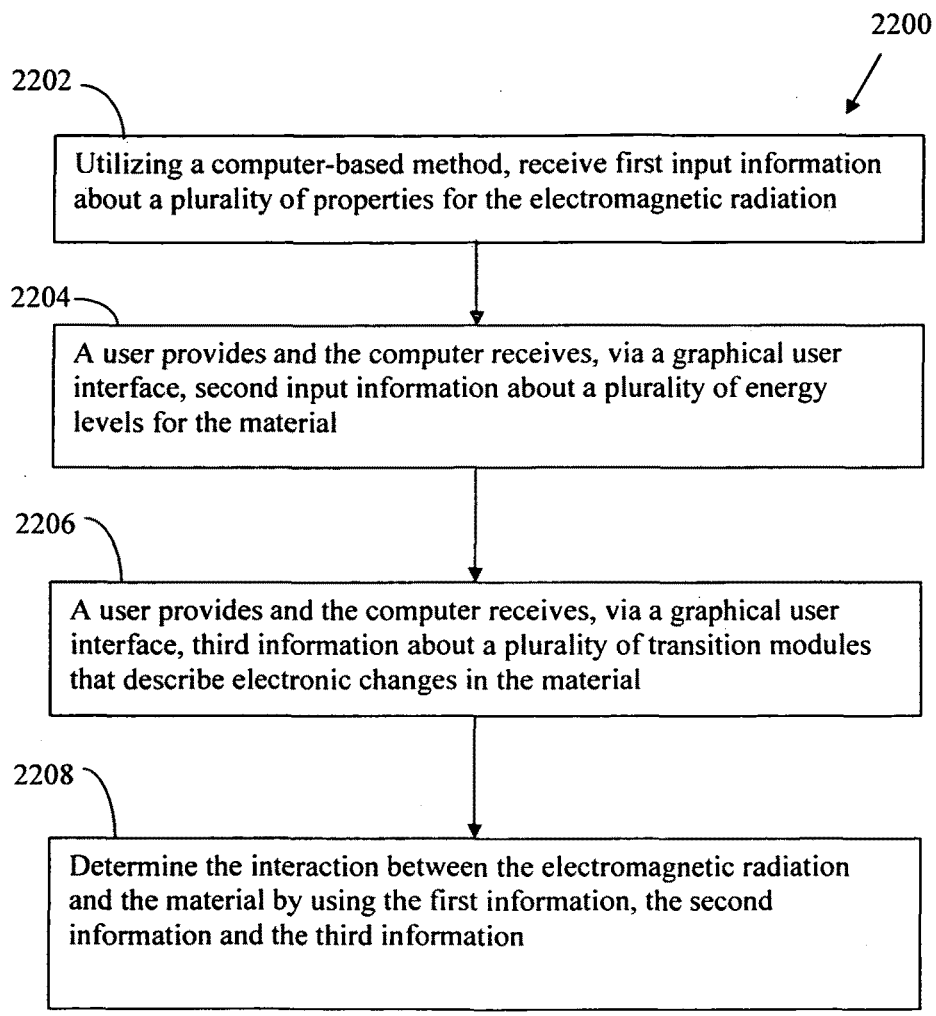
FIG. 22A is a flow chart for one embodiment of this invention.

The method is illustrated by flow chart 2200 shown in FIG. 22A. The flow chart lists a series of steps. The steps do not need to be done in the order listed. For example, the order of the first input information and the second input information may be reversed.

The method includes the following steps: Step 2202 is to receive first input information about a plurality of properties for the electromagnetic radiation. The first information can include, but is not limited to, the direction, the duration, the magnitude of the electric field as a function of the radial profile, the intensity of the electric field as a function of the radial profile and the wavelength of the electromagnetic radiation.

Step 2204 is to have a user provide and the computer receive, via a graphical user interface, second input information about a plurality of energy levels for the material. If the material has more than one composition or layer, the energy levels for each of the materials or layers should be provided.

Step 2206 is to have a user provide and the computer receive, via a graphical user interface, third input information about a plurality of transition modules that describe electronic changes in the material. The plurality of transition modules can include at least one absorption transition module and at least one relaxation transition module, the absorption transition module being associated with at least one absorption parameter and corresponding to an absorption process in the material and the relaxation transition module being associated with at least one relaxation parameter and corresponding to a relaxation process in the material. The plurality of transition modules can also include electron transfer transition modules, energy transfer transition modules and energy transfer upconversion transition modules. Examples of transition modules are illustrated in FIGS. 8, 9A, 9B, 10A, 10B, 12, 15 and 17 and are described in the text that is associated with the figures.

Step 2208 is to determine the interaction between the electromagnetic radiation and the material by using the first input information, the second input information and the third input information. Determining the interaction between the electromagnetic radiation and the material includes finding an electronic population of at least one of the plurality of energy levels or finding a transmission factor, an absorption factor or an emission factor for the electromagnetic radiation in the material.

Figure 22B:
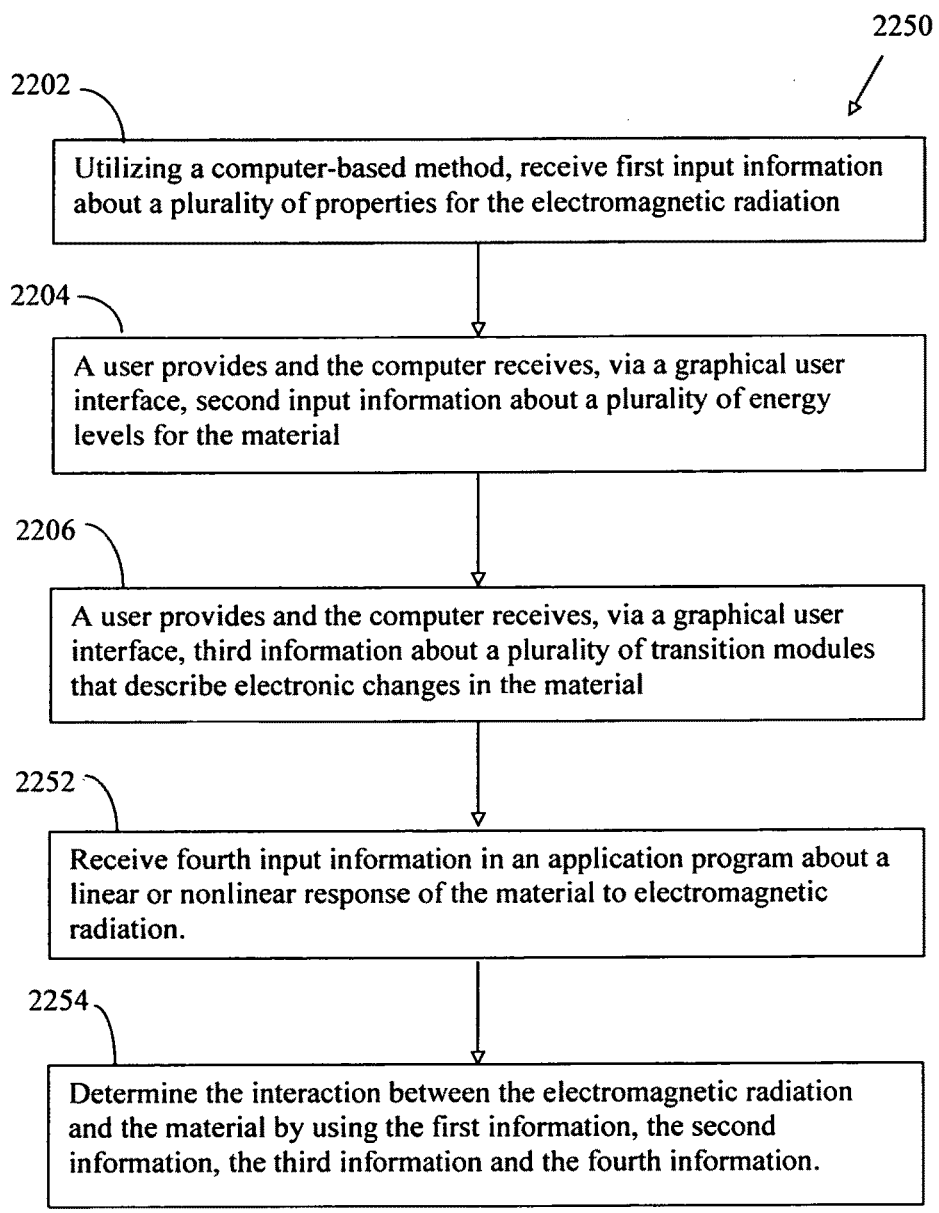
FIG. 22B is a flow chart for another embodiment of this invention.

Another embodiment of this invention is a computer-based method illustrated by flow diagram 2250 in FIG. 22B. Steps 2202, 2204 and 2206 are identical in flow diagrams 2200 and 2250. In flow diagram 2250, at step 2252 the computer receives a fourth input information about a linear or a nonlinear response of the material to the electromagnetic radiation. Then the step 2254 of determining the interaction between the electromagnetic radiation and the material uses the first input information, the second input information, the third input information and the fourth input information. An example of a linear response is diffraction or linear dispersion. Examples of nonlinear responses include, for example, a Kerr effect, a nonlinear dispersion effect or a nonlinear index of refraction effect resulting from a $Re\chi^{(3)}$ effect, a $Re\chi^{(5)}$ effect or a $Re\chi^{(2n+1)}$ effect of higher order with n>1.

Another embodiment of this invention is a computer-based software arrangement for analyzing an interaction between electromagnetic radiation and a material. The material may be a simple material having one composition or the material may have two or more different layers or the material may have at least one layer that has at least two different compositions.

Figure 23A:
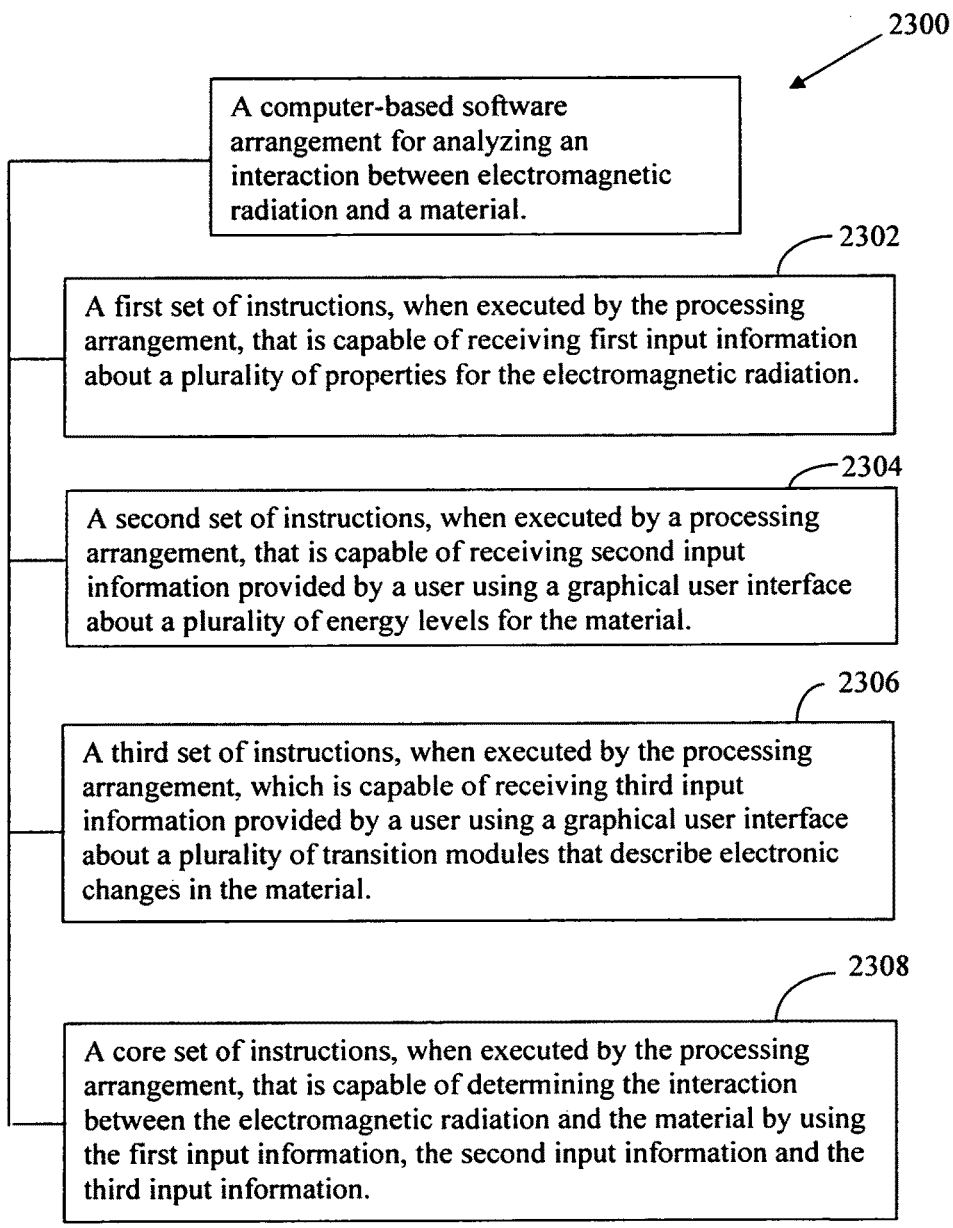
FIG. 23A illustrates a software embodiment of this invention.

The software arrangement 2300 is illustrated in FIG. 23A.

The computer-based software arrangement includes the following elements: The first element 2302 is a first set of instructions, when executed by the processing arrangement, which is capable of receiving first input information about a plurality of properties for the electromagnetic radiation. The first input information can include, but is not limited to, the direction, the duration, the magnitude of the electric field as a function of the radial profile, the intensity of the electric field as a function of the radial profile and the wavelength of the electromagnetic radiation.

The second element 2304 is a second set of instructions, when executed by a processing arrangement, that is capable of receiving second input information provided by a user using a graphical user interface about a plurality of energy levels for the material.

The third element 2306 is a third set of instructions, when executed by the processing arrangement, that is capable of receiving a third input information provided by a user using a graphical user interface about a plurality of transition modules that describe electronic changes in the material. The plurality of transition modules can include at least one absorption transition module and at least one relaxation transition module, the absorption transition module being associated with at least one absorption parameter and corresponding to an absorption process in the material and the relaxation transition module being associated with at least one relaxation parameter and corresponding to a relaxation process in the material. The plurality of transition modules can also include electron transfer transition modules, energy transfer transition modules and energy transfer up-conversion transition modules. Examples of transition modules are illustrated in FIGS. 8, 9A, 9B, 10A, 10B, 12, 15 and 17 and are described in the text that is associated with the figures.

Another element 2308 in software arrangement 2300 is a core set of instructions, when executed by the processing arrangement, which is capable of determining the interaction between the electromagnetic radiation and the material by using the first input information, the second input information and the third input information. Determining the interaction includes determining an electronic population of at least one of the plurality of energy levels and/or determining a transmission factor, an absorption factor or an emission factor for the electromagnetic radiation in the material.

Figure 23B:
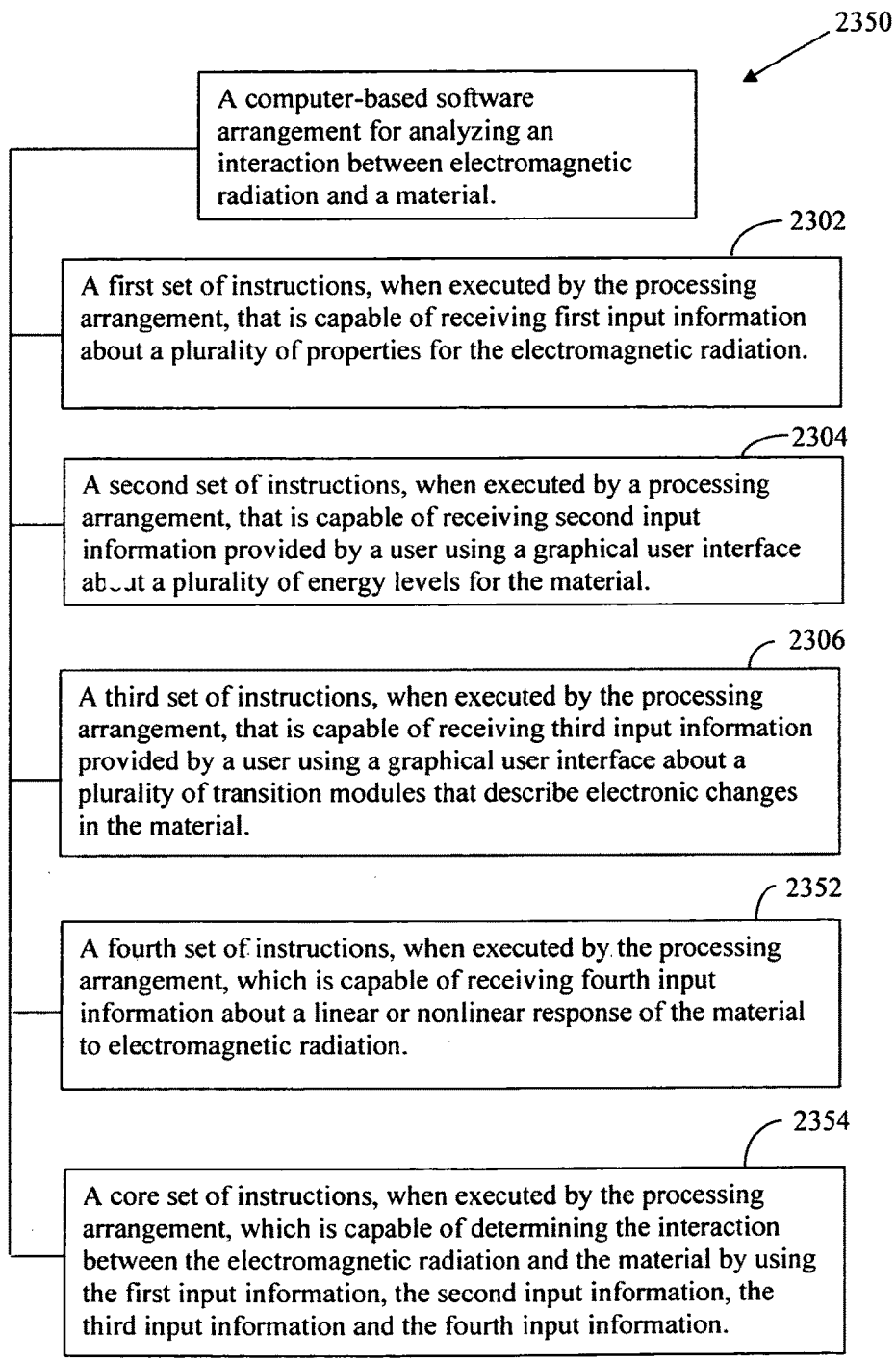
FIG. 23B illustrates another software embodiment of this invention.

FIG. 23B illustrates another embodiment of this invention. FIG. 23B illustrates an optional software arrangement 2350 that has an element 2352 that includes a fourth set of instructions, when executed by the processing arrangement, which is capable of receiving a fourth input information about a linear response or a nonlinear response of the material to the electromagnetic radiation. Elements 2302, 2304 and 2306 are identical in software arrangements 2300 and 2350. The core set of instructions 2354, when executed by the processing arrangement, is then capable of determining the interaction between the electromagnetic radiation and the material by using the first input information, the second input information, the third input information and the fourth input information. An example of a linear response is diffraction or linear dispersion. Examples of nonlinear responses include, for example, a Kerr effect, a nonlinear dispersion effect, or a nonlinear index of refraction effect resulting from a $\text{Re}\chi^{(3)}$ effect, a $\text{Re}\chi^{(5)}$ effect or a $\text{Re}\chi^{(2n+1)}$ effect of higher order with $n>1$.

In FIGS. 23A and 23B, the processing arrangement can optionally include two or more processing units. A first processing unit can be utilized for executing the core set of instructions that is capable of determining an electronic population of at least one of the plurality of energy levels or is capable of determining a transmission factor, an absorption factor or an emission factor for the electromagnetic radiation in the material. A second processing unit can be utilized for controlling the graphical user interface. The second processing unit executes the second and third sets of instructions that are capable of receiving second and third input information, provided by the user utilizing a graphical user interface, about a plurality of energy levels and about a plurality of transition modules that describe electronic changes in the material.

While the invention has been described in conjunction with specific embodiments and examples, it is evident to those skilled in the art that many alternatives, modifications and variations will be apparent in light of the foregoing description. Accordingly, the invention is intended to embrace all such alternatives, modifications and variations as fall within the spirit and scope of the appended claims.

What is claimed is:

1. A system for analyzing an interaction between electromagnetic radiation and a material, the system comprising:
   a processing arrangement for executing computer programs;
   a display unit having at least one display screen;
   a memory unit that stores an application program that includes first executable instructions operable on the system for determining the interaction between the electromagnetic radiation and the material using at least one input from the display unit, said application program using at least one propagation equation and at least one rate equation and second executable instructions operable on the system for displaying a graphical user interface on the display unit, the second executable instructions including instructions to:
      show on the display unit a toolbox having a plurality of icons, the plurality of icons including at least a first icon representing a plurality of energy levels for the material and at least a second icon representing an element of a plurality of transition modules for the material, wherein the second icon has at least one associated numerical parameter used in at least one matrix included in the at least one rate equation;
      show on the display unit a designer window configured to present the plurality of energy levels for the material and the plurality of transition modules for the material;
      detect movement of a copy of the first icon from the toolbox to the designer window, thereby modifying within the designer window the plurality of energy levels, or detect movement of a copy of the second icon from the toolbox to the designer window, thereby modifying within the designer window the plurality of transition modules for the material; and
      receive the at least one associated numerical parameter for input into said at least one matrix of the at least one rate equation; and
   a storage unit that stores the results generated by the application program wherein the second executable instructions include instructions to show on the display unit one or a plurality of designer windows designed to present the plurality of energy levels for each composition in a composite material with at least two different compositions and the plurality of transition modules for each composition in the composite material with at least two different compositions.

2. The system as in claim 1, wherein the processing arrangement includes a first processing unit for executing the first executable instructions operable on the system for determining the interaction between the electromagnetic radiation and the material and a second processing unit for executing the second executable instructions operable on the system for displaying the graphical user interface on the display unit.

3. The system as in claim 1, whereby the first executable instructions for determining the interaction between the electromagnetic radiation and the material include instructions for finding an electronic population of at least one of the plurality of energy levels in the material or finding a transmission factor, an absorption factor or an emission factor for the electromagnetic radiation in the material.

4. A system for analyzing an interaction between electromagnetic radiation and a material, the system comprising:
   a processing arrangement for executing computer programs;
   a display unit having at least one display screen;
   a memory unit that stores an application program that includes first executable instructions operable on the system for determining the interaction between the electromagnetic radiation and the material using at least one input from the display unit, said application program using at least one propagation equation and at least one rate equation and second executable instructions operable on the system for displaying a graphical user interface on the display unit, the second executable instructions including instructions to:
      show on the display unit a toolbox having a plurality of icons, the plurality of icons including at least a first icon representing a plurality of energy levels for the material and at least a second icon representing an element of a plurality of transition modules for the material, wherein the second icon has at least one associated numerical parameter used in at least one matrix included in the at least one rate equation;
      show on the display unit a designer window configured to present the plurality of energy levels for the material and the plurality of transition modules for the material;
      detect movement of a copy of the first icon from the toolbox to the designer window, thereby modifying within the designer window the plurality of energy levels, or detect movement of a copy of the second icon from the toolbox to the designer window, thereby modifying within the designer window the plurality of transition modules for the material; and
      receive the at least one associated numerical parameter for input into said at least one matrix of the at least one rate equation; and
   a storage unit that stores the results generated by the application program wherein the second executable instructions include instructions to show on the display unit one or a plurality of designer windows designed to present a virtual sample of a layered material with at least two different layers.

5. A computer-based method for analyzing an interaction between electromagnetic radiation and a material using at least one propagation equation and at least one rate equation, the method comprising:

receiving at a computer a first input information about a plurality of properties of the electromagnetic radiation;

receiving at the computer from a graphical user interface a second input information about a plurality of energy levels for the material;

receiving at the computer from the graphical user interface a third input information about a plurality of transition modules that describe transitions of electrons between energy levels of the material, said third input information including numerical parameters to be incorporated as elements in at least one matrix of the at least one rate equation; and determining with a program executing on the computer the interaction between the electromagnetic radiation and the material using the first input information, the second input information, the third input information, and the at least one propagation equation and the at least one rate equation to determine an electronic population for at least one of the plurality of energy levels or a transmission factor, an absorption factor or an emission factor for the electromagnetic radiation in the material;

wherein the graphical user interface comprises a toolbox having a plurality of icons, the plurality of icons including a first icon representing an energy level in the material and a second icon representing a transition module for the material, and a designer window configured to present a plurality of first icons and a plurality of second icons and the second and third inputs are received at the computer when the computer detects that an icon has been moved from the toolbox to the designer window; and wherein the material has at least two different compositions or two different layers and the designer window is configured to present a representation of the plurality of energy levels and a representation of the plurality of transition modules for each of the different compositions or different layers.

6. A system for analyzing an interaction between electromagnetic radiation and a material, the system comprising:

a processing arrangement for executing computer programs;

a display unit having at least one display screen;

a memory unit that stores an application program that includes first executable instructions operable on the system for determining the interaction between the electromagnetic radiation and the material using at least one input from the display unit, and second executable instructions operable on the system for displaying a graphical user interface on the display unit, the second executable instructions including instructions to:

show on the display unit a toolbox having a plurality of icons, the plurality of icons including a first icon representing an energy level for the material and at least a second icon representing an element of a plurality of transition modules for the material, wherein the second icon has at least one associated parameter used in the application program;

show on the display unit a designer window configured to present the plurality of energy levels for the material and the plurality of transition modules for the material;

detect movement of a copy of the first icon from the toolbox to the designer window, thereby modifying within the designer window the plurality of energy levels, or detect movement of a copy of the second icon from the toolbox to the designer window, thereby modifying within the designer window the plurality of transition modules for the material; and receive at least one associated parameter for input into the application program; and a storage unit that stores the results generated by the application program;

wherein the second executable instructions include instructions to show on the display unit one or a plurality of designer windows designed to present the plurality of energy levels for each composition in a composite material with at least two different compositions and the plurality of transition modules for each composition in the composite material with at least two different compositions.

* * * * *